US008930207B2

(12) United States Patent
Keravich et al.

(10) Patent No.: US 8,930,207 B2
(45) Date of Patent: Jan. 6, 2015

(54) MEDICAL PRODUCT DISPENSING SYSTEMS AND METHODS

(75) Inventors: Daniel Paul Keravich, Rockville, MD (US); Richard Alexander McGregor, Parsippany, NJ (US); George Michael Quesnelle, Moon Township, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 563 days.

(21) Appl. No.: 12/265,888

(22) Filed: Nov. 6, 2008

(65) Prior Publication Data

US 2009/0125324 A1 May 14, 2009

Related U.S. Application Data

(60) Provisional application No. 61/002,360, filed on Nov. 8, 2007, provisional application No. 61/068,909, filed on Mar. 11, 2008.

(51) Int. Cl.
*G06Q 10/00* (2012.01)
*G06Q 50/22* (2012.01)
*G06F 19/00* (2011.01)
*G07F 17/00* (2006.01)

(52) U.S. Cl.
CPC ............ *G07F 17/0092* (2013.01); *G06Q 50/22* (2013.01); *G06F 19/3462* (2013.01)
USPC .......................................................... 705/2

(58) Field of Classification Search
CPC ......................................... G06Q 50/22–50/24
USPC ....................................................... 705/2–3
See application file for complete search history.

(56) References Cited

U.S. PATENT DOCUMENTS

| 4,845,636 A | 7/1989 | Walker ........................... 364/479 |
| 4,847,764 A | 7/1989 | Halvorson ............... 364/413.02 |
| 5,139,384 A | 8/1992 | Tuttobene ..................... 414/281 |
| 5,190,185 A | 3/1993 | Blechl ............................... 221/1 |
| 5,291,191 A | 3/1994 | Moore et al. ............. 340/825.35 |

(Continued)

FOREIGN PATENT DOCUMENTS

| DE | 10348751 | 4/2004 |
| EP | 1431902 | 6/2004 |

(Continued)

OTHER PUBLICATIONS

Evincii, PharmAssist, 2006-2008.

(Continued)

*Primary Examiner* — Robert Sorey
(74) *Attorney, Agent, or Firm* — Ohlandt, Greeley, Ruggiero & Perle, LLP

(57) ABSTRACT

Methods and systems for transferring restricted distribution medical products to an over-the-counter general sales environment are provided. Methods and systems of dispensing non-prescription, behind-the-counter medical products from a vending machine in a general sales location are also provided. In some embodiments, methods and systems are provided for dispensing a medical product from a vending machine in a general sales location based, at least in part, on biometric data collected from the purchaser and, in some instances, based on self-selection and/or de-selection criteria, is provided. Further, methods and systems of switching prescription medical products to non-prescription, over-the-counter medical products are provided.

32 Claims, 17 Drawing Sheets

(56) References Cited

U.S. PATENT DOCUMENTS

| | | | |
|---|---|---|---|
| 5,377,864 A | 1/1995 | Blechl et al. | 221/2 |
| 5,445,294 A | 8/1995 | Gardner et al. | 221/1 |
| 5,713,485 A | 2/1998 | Liff et al. | 221/2 |
| 5,722,526 A | 3/1998 | Sharrard | 194/346 |
| 5,797,515 A | 8/1998 | Liff et al. | 221/2 |
| 5,852,590 A | 12/1998 | De la Huerga | 368/10 |
| 6,032,155 A | 2/2000 | De la Huerga | 707/104 |
| 6,045,501 A | 4/2000 | Elsayed et al. | 600/300 |
| 6,068,156 A | 5/2000 | Liff et al. | 221/7 |
| 6,116,461 A | 9/2000 | Broadfield et al. | 221/98 |
| 6,119,932 A | 9/2000 | Maloney | |
| 6,148,091 A | 11/2000 | DiMaria | 382/115 |
| 6,283,322 B1 | 9/2001 | Liff et al. | 221/7 |
| 6,315,720 B1 | 11/2001 | Williams et al. | 600/300 |
| 6,330,491 B1 | 12/2001 | Lion et al. | 700/237 |
| 6,338,007 B1 | 1/2002 | Broadfield et al. | 700/231 |
| 6,403,897 B1 | 6/2002 | Bluth | |
| 6,428,124 B1 | 8/2002 | Bluth | |
| 6,438,451 B1 | 8/2002 | Lion et al. | 700/237 |
| 6,453,302 B1 | 9/2002 | Johnson | |
| 6,470,234 B1 | 10/2002 | McGrady et al. | 700/241 |
| 6,471,089 B2 | 10/2002 | Liff et al. | 221/13 |
| 6,511,435 B1 | 1/2003 | Bluth | |
| 6,516,997 B1 | 2/2003 | Tanazawa et al. | 235/380 |
| 6,523,741 B1 | 2/2003 | DiMaria et al. | 235/375 |
| 6,529,801 B1 | 3/2003 | Rosenblum et al. | 700/237 |
| 6,532,399 B2 | 3/2003 | Mase | 700/237 |
| 6,539,281 B2 | 3/2003 | Wan et al. | 700/236 |
| 6,539,282 B2 | 3/2003 | Metcalf et al. | 700/237 |
| 6,561,976 B2 | 5/2003 | Elsayed et al. | 600/300 |
| 6,564,121 B1 | 5/2003 | Wallace et al. | 700/237 |
| 6,581,798 B2 | 6/2003 | Liff et al. | 221/13 |
| 6,611,733 B1 | 8/2003 | De la Huerga | 700/236 |
| 6,625,952 B1 | 9/2003 | Chudy et al. | 53/168 |
| 6,640,159 B2 | 10/2003 | Holmes et al. | 700/244 |
| 6,650,964 B2 | 11/2003 | Spano et al. | 700/237 |
| 6,692,436 B1 | 2/2004 | Bluth | |
| 6,697,704 B2 | 2/2004 | Rosenblum | 700/232 |
| 6,711,465 B2 | 3/2004 | Tomassi | 700/236 |
| 6,735,497 B2 | 5/2004 | Wallace et al. | 700/231 |
| 6,766,218 B2 | 7/2004 | Rosenblum et al. | 700/235 |
| 6,767,326 B2 | 7/2004 | Elsayed et al. | 600/300 |
| 6,776,304 B2 | 8/2004 | Liff et al. | 221/2 |
| 6,814,254 B2 | 11/2004 | Liff et al. | 221/7 |
| 6,814,255 B2 | 11/2004 | Liff et al. | 221/13 |
| 6,850,816 B2 | 2/2005 | Garratt et al. | 700/237 |
| 6,871,783 B2 | 3/2005 | Kaafarani et al. | 235/380 |
| 6,892,941 B2 | 5/2005 | Rosenblum | 235/383 |
| 6,908,432 B2 | 6/2005 | Elsayed et al. | 600/300 |
| 7,006,893 B2 | 2/2006 | Hart et al. | 700/237 |
| 7,040,504 B2 | 5/2006 | Broadfield et al. | 221/98 |
| 7,072,738 B2 | 7/2006 | Bonney et al. | 700/237 |
| 7,080,755 B2 | 7/2006 | Handfield et al. | 221/13 |
| 7,123,989 B2 | 10/2006 | Pinney et al. | 700/237 |
| 7,151,982 B2 | 12/2006 | Liff et al. | 700/241 |
| 7,262,698 B1 | 8/2007 | Frederick et al. | 340/545.6 |
| 7,263,410 B1 | 8/2007 | Frederick et al. | 700/236 |
| 7,269,476 B2 | 9/2007 | Ratnakar | 700/236 |
| 7,286,900 B1 | 10/2007 | Frederick et al. | 700/242 |
| 7,349,858 B1 | 3/2008 | McGrady et al. | 705/3 |
| 7,353,080 B2 | 4/2008 | Walker | |
| 7,374,083 B2 | 5/2008 | Estruth et al. | 235/381 |
| 7,734,371 B2* | 6/2010 | Garneau, III | 700/236 |
| 7,860,604 B2* | 12/2010 | Frankel | 700/236 |
| 2002/0062175 A1* | 5/2002 | Lion | 700/237 |
| 2002/0087413 A1 | 7/2002 | Mahaffy et al. | 705/16 |
| 2003/0060926 A1 | 3/2003 | Yuyama et al. | 700/237 |
| 2003/0074225 A1* | 4/2003 | Borsand et al. | 705/3 |
| 2003/0195654 A1* | 10/2003 | Spano et al. | 700/237 |
| 2003/0216831 A1 | 11/2003 | Hart et al. | |
| 2004/0010340 A1 | 1/2004 | Guindulain Vidondo | 700/237 |
| 2004/0019794 A1* | 1/2004 | Moradi et al. | 713/185 |
| 2004/0143445 A1 | 7/2004 | Sheem | |
| 2004/0153421 A1 | 8/2004 | Robinson | 705/75 |
| 2004/0158351 A1 | 8/2004 | Rivalto | 700/237 |
| 2005/0049746 A1 | 3/2005 | Rosenblum | 700/232 |
| 2005/0065645 A1 | 3/2005 | Liff et al. | |
| 2005/0075907 A1* | 4/2005 | Rao | 705/2 |
| 2005/0154491 A1 | 7/2005 | Anderson et al. | 700/236 |
| 2005/0187656 A1 | 8/2005 | Walker et al. | 700/232 |
| 2005/0192705 A1 | 9/2005 | Pinney et al. | 700/241 |
| 2005/0251289 A1 | 11/2005 | Bonney et al. | 700/244 |
| 2006/0058918 A1 | 3/2006 | Handfield et al. | 700/236 |
| 2006/0093934 A1 | 5/2006 | Roberts | |
| 2006/0155607 A1* | 7/2006 | Bahir | 705/26 |
| 2006/0195222 A1 | 8/2006 | Ringer et al. | 700/240 |
| 2006/0213917 A1 | 9/2006 | Handfield et al. | 221/13 |
| 2006/0219730 A1 | 10/2006 | Handfield et al. | 221/13 |
| 2006/0241806 A1 | 10/2006 | Handfield et al. | 700/231 |
| 2006/0247823 A1 | 11/2006 | Boucher | 700/241 |
| 2006/0259187 A1 | 11/2006 | Berg et al. | 700/231 |
| 2006/0259188 A1 | 11/2006 | Berg et al. | 700/231 |
| 2006/0265102 A1 | 11/2006 | Bain | 700/237 |
| 2006/0266823 A1 | 11/2006 | Passen et al. | 235/381 |
| 2007/0043469 A1* | 2/2007 | Draper | 700/231 |
| 2007/0093934 A1* | 4/2007 | Garneau | 700/236 |
| 2007/0095901 A1 | 5/2007 | Illingworth et al. | 235/381 |
| 2007/0100696 A1 | 5/2007 | Illingworth et al. | 705/14 |
| 2007/0150092 A1 | 6/2007 | Ohmura et al. | 700/231 |
| 2007/0156282 A1 | 7/2007 | Dunn | 700/244 |
| 2007/0162184 A1 | 7/2007 | Pinney et al. | 700/241 |
| 2007/0187422 A1 | 8/2007 | Handfield et al. | 221/13 |
| 2007/0293982 A1* | 12/2007 | Rosenblum | 700/235 |
| 2007/0293983 A1 | 12/2007 | Butler et al. | 700/237 |
| 2008/0015897 A1* | 1/2008 | Moradi et al. | 705/2 |
| 2008/0029531 A1 | 2/2008 | Handfield et al. | 221/7 |
| 2008/0029532 A1 | 2/2008 | Handfield et al. | 221/7 |
| 2008/0051933 A1 | 2/2008 | Vrachan et al. | 700/231 |
| 2008/0051935 A1 | 2/2008 | Handfield et al. | 700/237 |
| 2008/0058985 A1* | 3/2008 | Alcov | 700/234 |
| 2008/0065546 A1 | 3/2008 | Ramachandran | 705/44 |
| 2008/0071421 A1 | 3/2008 | Silverbrook et al. | 700/231 |
| 2008/0077274 A1 | 3/2008 | Kim | 700/237 |
| 2008/0077440 A1 | 3/2008 | Doron | |
| 2008/0199407 A1* | 8/2008 | Slater et al. | 424/10.3 |
| 2008/0215463 A1 | 9/2008 | Estruth et al. | 705/28 |

FOREIGN PATENT DOCUMENTS

| | | |
|---|---|---|
| EP | 1431902 A2 * | 6/2004 |
| JP | 8241455 | 9/1996 |
| JP | 10334326 | 12/1998 |
| JP | 10334326 A | 12/1998 |
| JP | 2000155817 | 6/2000 |
| JP | 2001052064 | 2/2001 |
| JP | 2002042214 | 2/2002 |
| JP | 2002269623 | 9/2002 |
| JP | 2002342817 | 11/2002 |
| JP | 2003006720 | 1/2003 |
| JP | 2003114932 A | 4/2003 |
| JP | 2004341983 A | 12/2004 |
| JP | 2004362179 A | 12/2004 |
| JP | 2005018489 A | 1/2005 |
| RU | 2325100 | 5/2007 |
| WO | WO2005/098709 | 10/2005 |
| WO | 2006036712 | 4/2006 |

OTHER PUBLICATIONS

Accutane, pp. 1-46, 2000-2007.

STEPSprogram, Apr. 2008.

International search report for PCT/US08/82564.

Imigran checklist and instructions, May 2006.

Australian Office Action dated Jul. 17, 2012 for Australian application No. 2008-323993.

Decision of Grant dated Jan. 23, 2012 for Russian application No. 2010123012 with English translation.

Australian Examination Report dated Feb. 11, 2011 for Australian application No. 2008323993.

Mexican Office Action dated Aug. 23, 2011 for Mexican application No. MX/A/2010/005090 with English translation.

(56) References Cited

OTHER PUBLICATIONS

Japanese Office Action (with English translation) dated Jan. 8, 2013 for Japanese application No. 2010-533226.

Chinese Office Action (English translation) dated Feb. 28, 2013 for Chinese application No. 200880124312.6.
Chinese Office Action (English translation) dated Nov. 14, 2013 for Chinese application No. 200880124312.6.

* cited by examiner

MEDICAL PRODUCT DISPENSING SYSTEMS AND METHODS

CROSS REFERENCE TO RELATED APPLICATIONS

This application claims the benefit of U.S. Provisional Application Ser. No. 61/002,360, filed Nov. 8, 2007, and claims the benefit of U.S. Provisional Application Ser. No. 61/068,909, filed Mar. 11, 2008, the contents of both of which are incorporated by reference herein in their entirety.

BACKGROUND OF THE INVENTION

1. Field of the Invention

The present disclosure relates to medicines, nutraceuticals, and medical devices (hereinafter collectively referred to as "medical products") dispensing systems and methods. More particularly, the present disclosure relates to systems and methods for dispensing medical products from a vending machine using a self-selection algorithm and, in some embodiments, a de-selection algorithm, which eliminate the need for interaction between the purchaser and a licensed practitioner. Further, the present disclosure relates to methods of providing a risk management tool for switching prescription medical products to non-prescription, over-the-counter status. Still further, the present disclosure relates to systems and methods that provide greater access to over-the-counter medical products that have sales or distribution restrictions due to public safety and/or public health concerns.

2. Description of Related Art

Drugs, vaccines, biologics, and pharmaceutical products (hereinafter individually and collectively referred to as "medicines") are commonly used to cure, treat and/or mitigate a variety of human and animal aliments and maladies. For purposes of dispensing these products in the United States, medicines are generally divided by Section 503(b)(1) of the Food, Drug, and Cosmetic Act into two classifications, namely prescription classification and a non-prescription classification. More specifically, the Food and Drug Administration (FDA) requires a prescription for the dispensing of any drug that is not safe for use except under the supervision of a practitioner licensed by law to administer such drug. Thus, the FDA can designate a medicine with a non prescription status when the FDA finds that prescription dispensing is not necessary for the protection of the public health by reason of the drug's toxicity or other potentiality for harmful effect, or the method of its use, or the collateral measures necessary to its use, and the drug is safe and effective for use in self-medication as directed in proposed labeling.

Due to the highly regulated nature of medicines in the prescription classification, these prescription medicines are mostly dispensed from a licensed pharmacy. Typically, the medicines are controlled and stored in a restricted area of a pharmacy, namely behind-the-counter in the pharmacy, such that the dispensing of the medicine from a pharmacy can only be performed by or under the supervision of a pharmacist (hereinafter referred to as a "licensed practitioner").

In contrast, and due to evidence that suggests that there are adequate controls and labeling in place for the safe and effective use in an over-the-counter setting, prescription medicines have typically been moved over-the-counter (OTC) from the restricted sales area and into the general sales areas in the pharmacy or other retail general sales location. As used herein, the term "general sales" area or location shall mean any area where access to the medicine is not restricted. As such, the general sales area or location can include the areas inside of a store, but not behind-the-counter of the pharmacy or behind-the-counter of the point-of-sale, and can include areas outside of the store.

In addition to the regulations placed on medicines by the FDA, the distribution of some medicines are also restricted or regulated by one or more federal and or state governmental agencies such as the Department of Justice (DOJ), the Drug Enforcement Agency (DEA) or individual State Boards of Pharmacy.

For example, pseudoephedrine (PSE) is a medicine that has non-prescription status, and is commonly used as a decongestant. However, PSE can also be used in the production of illicit and illegal drugs such as, but not limited to, methamphetamine. As such, governmental agencies have required that merchants or regulated sellers of PSE and PSE containing products regulate or restrict the distribution of PSE and PSE containing products. The restriction of PSE and PSE containing products typically includes moving the location of such products to a behind-the-counter setting in order to track the sales of such products. The compliance for documenting sales information and purchaser information is typically performed at the point-of-sale. Accordingly, although PSE is a non-prescription medicine, which would otherwise be made available in an over-the-counter setting, other agency regulations and distribution restrictions related to its sale have caused retailers to move this medicine to a behind-the-counter setting to capture the compliance information, Thus, state authorities have the ability to schedule any over-the-counter medicine and to move these medicines to a behind-the-counter setting for reasons of public health.

More recently, certain medicines have been classified as dual status medicines in the United States. Dual status medicines are medicines that have a non-prescription classification for certain portions of the population, but maintain a prescription classification for other portions of the population. For example, the emergency oral contraceptive Plan-B can be dispensed without a prescription to women over the age of 18, but is dispensed to women under the age of 18 only with a prescription. Accordingly, other medicines, such as the aforementioned oral contraceptive, have both a prescription and non-prescription classification. These dual status medicines are available only behind-the-counter of the pharmacy as certain criteria, such as age verification by the licensed practitioner, must be met before dispensing without a prescription.

Most countries regulate the distribution of medicines in a manner similar to the regulations for dispensing medicines in the United States discussed above.

For example, Australia utilizes a medicine distribution system that classifies the available distribution system into four different categories or schedules, namely Unscheduled, Schedule 4, Schedule 3, or Schedule 2. It should be noted that the term schedule as used in the Australian classifications system is not the same as that used under the U.S. system and referenced under U.S.C. 812 and the Controlled Substance Act.

In Australia, unscheduled medicines are general sale products that are available without prescription or interaction with a pharmacist and, thus, are typically available over-the-counter at any retail location. In contrast, medicines classified as Schedule 4 and Schedule 3 are located behind-the-counter, while Schedule 2 are located in front of the pharmacy counter. More particularly, medicines classified as "Schedule 4 medicines" are available by prescription only and are available for distribution from behind-the-counter by a pharmacist in a pharmacy location. Medicines classified as "Schedule 3 medicines" are available without a prescription (i.e., a nonprescription medicine), but can be supplied only by a pharmacist in a pharmacy location. Thus, Schedule 3 medicines are available for distribution from behind-the-counter to allow for the necessary pharmacist-patient interaction. Medicines classified as "Schedule 2 medicines" are available without a prescription, but may require advice from a pharmacist prior to dispensing. As such, Schedule 2 medicines are also available for distribution and access from in front-the-counter, and to provide the opportunity for a pharmacist-patient interaction at a pharmacy location only.

As another example, the United Kingdom utilizes a medicine distribution system that classifies the medicine into one of three categories, namely general sales, pharmacy sales, and prescription sales. As the name suggest, general sales medicines are available without prescription or need for any interaction with a pharmacist and, thus, are available over-the-counter in the general sales area of a retail outlet. Pharmacy sales are available without prescription, but provide a means for an interaction with a pharmacist and, thus, are available behind-the-counter of the pharmacy. Further, prescription sales are available only with a prescription and, thus, are only available behind-the-counter of the pharmacy.

As seen from the discussion above, the distribution of medicines is typically based on a classification system, which generally results in the medicine either being available without distribution restrictions over-the-counter, which does not require interaction with doctor or pharmacist, or being available with distribution restrictions behind-the counter, which requires interaction with a pharmacist, or other employee.

It has been determined by the present disclosure that the distinction between medicines available with restrictions "behind-the-counter" and those available with or without restriction "over-the-counter" is important to the retail outlet or merchant selling the medicine. More specifically, "over-the-counter" medicines without restrictions do not require licensed pharmacy sites or any interactions with an employee or pharmacist when being purchased by a purchaser. In contrast, "behind-the-counter" medicines and age restricted over the counter medicines do require interaction with an employee when being purchased by a purchaser.

In addition to regulations placed on medicines discussed in detail above, the distribution of many medical devices such as, but not limited to, hypodermic needles, HIV tests, certain orthopedic devices are also regulated. For example, many states require the sale of hypodermic needles to be made from behind-the-counter and/or only to persons over a predetermined age. In addition, some medical devices are only available with a prescription. Thus, access to many non-medicinal medical devices are faced with similar distribution difficulties discussed hereinabove.

Further, many products fall into a more general class of products referred to herein as "nutraceuticals", which includes products such as, but not limited to, nutritional supplements, functional foods, dietary supplements, vitamins, botanicals, medical foods, and others. It is contemplated that one or more of the aforementioned and other nutraceuticals may have a restricted distribution status imposed thereon by a regulating body, by the manufacturer, by the retail outlet, and any combinations thereof.

In addition, the distinction between medical products available "behind-the-counter" and those available "over-the-counter" is important to the consumers who have a desire to use or select certain medical products. For instance, the over-the-counter medical products that do not require interaction with an employee and makes the medical products more easily obtainable by the consumer.

Accordingly, it has been determined by the present disclosure that there is a continuing need for systems and methods for dispensing medical products having a non-prescription status without the need for the additional access restraints and restrictions traditionally associated with such behind-the-counter and pharmacy sales only. Further, it has been determined by the present disclosure that there is a need for methods of switching prescription medical products to non-prescription status using an electronic vending machine as a means to aid, assist and restrict access to ensure the safe and effective use of such prescription products in an over-the-counter environment.

Further, it has been determined by the present disclosure that there is a continuing need for systems and methods for dispensing medicines having a non-prescription status without the need for the additional access restraints and restrictions by retailers who use physical barriers or place medical products and devices behind the counter or under the control of a sales employee in order to restrict access due to concerns of theft.

BRIEF SUMMARY OF THE INVENTION

The present disclosure provides methods for dispensing non-prescription, behind-the counter medical products (i.e., medicines, nutraceuticals, and medical devices) using a vending machine in conjunction with an electronic self-selection process.

The present disclosure also provides methods for dispensing non-prescription, behind-the counter medical products from a vending machine in a general sales location using a vending machine in conjunction with both selecting and de-selecting processes.

In some embodiments, the present disclosure provides methods of dispensing non-prescription, behind-the counter medical products from a vending machine in a general sales location using a self-selecting step that is based, at least in part, on biometric data. The biometric data can be locally inputted by purchaser (manually or by attaching a biometric measuring device) or retrieved by the vending machine from a reference lab or other external source.

In still other embodiments, the present disclosure provides systems and methods for switching prescription medical products to non-prescription, over-the-counter status. Here, the systems and methods of the present disclosure provide for interactive compliance to the collateral measures necessary to meet the requirements set forth by the FDA for switching such prescription medicines.

A method for dispensing restricted distribution medical products is provided. The method includes identifying a particular medical product having a distribution restricted status; placing a vending machine in a general sales location, the vending machine having a user-interface in communication with a controller; storing a supply of the particular medical product in the vending machine; storing an electronic self-selection process on the controller; and controlling the vending machine, via the controller, to dispense a first sales unit of the particular medical product only if a purchaser successfully completes the self-selection process for an initial purchase request for the particular medical product via the user interface.

A method of dispensing non-prescription, behind-the-counter medical products from a vending machine in a general sales location is also provided. The method includes accepting a purchase request at a vending machine from a purchaser for a particular non-prescription, behind-the-counter medical product; determining if the purchase request is an initial purchase request or a subsequent purchase request by the purchaser for the particular medical product; accessing a self-selection algorithm for the particular medical product if the purchase request is the initial purchase request; accessing a de-selection algorithm for the particular medical product if the purchase request is the subsequent purchase request; requiring the purchaser to input an answer to each of a plurality of questions generated by the self-selection algorithm or the de-selection algorithm; and controlling the vending machine, via the self-selection algorithm or the de-selection algorithm, to dispense or not dispense the particular medical product based the answers.

In some embodiments, a method of dispensing a medical product from a vending machine in a general sales location is provided. The method includes accepting a purchase request at a vending machine from a purchaser for a particular medical product; accessing a dispensing algorithm for the particular medical product; requiring the purchaser to input an answer to each of a plurality of questions generated by the dispensing algorithm; collecting biometric data from the purchaser; and determining whether or not to dispense the particular medical product based on the answers and based, at least in part, on the biometric data.

A medical product dispensing system is also provided that includes a vending machine, one or more user-interface devices, and a controller in communication with the vending machine and the one or more user-interface devices. The vending machine defines a storage space that can receive one or more restricted distribution medical products and one or more unrestricted distribution medical products therein. The system further includes a self-selection algorithm resident on the controller for each of the restricted distribution medical products in the storage space. The controller, upon selection of a particular restricted distribution medical product by a purchaser via the one or more user-interface devices, is configured to determine whether the selection of the particular restricted distribution medical product is a first request or a second or subsequent request for the particular restricted distribution medical product. The controller requires the purchaser to complete the self-selection algorithm if the request is the first request. The controller dispenses the particular restricted distribution medical product only if the purchaser successfully completes the self-selection algorithm.

A method for distributing a medical product is provided that includes: providing a controller having a matching algorithm resident thereon; allowing a purchaser to access to the matching algorithm; controlling the matching algorithm to provide a plurality of exemplary symptoms or disease-states to the purchaser via at least one data entry and communication device in visual or auditory form; allowing the user to select one or more symptoms or disease-states from the plurality of exemplary symptoms or disease-states when the one or more symptoms or disease-states match those currently being experienced by the purchaser; and controlling the matching algorithm to provide a list of one or more appropriate medical products for the one or more symptoms or disease-states selected.

A method for distributing a medical product is provided that includes: storing an electronic self-selection process related to the medical product on a controller; storing an electronic de-selection process related to the medical product on the controller; allowing a potential purchaser of the medical product to access the electronic self-selection and de-selection processes; controlling the controller via the electronic self-selection process to provide an transaction record for the medical product only if the potential purchaser successfully completes the self-selection process for an initial purchase request of the medical product; and controlling the controller via the electronic de-selection process to provide the transaction record for the medical product only if the potential purchaser successfully completes the de-selection process for a second or subsequent purchase request of the medical product.

The above-described and other features and advantages of the present disclosure will be appreciated and understood by those skilled in the art from the following detailed description, drawings, and appended claims.

DETAILED DESCRIPTION OF THE INVENTION

Figure 1:
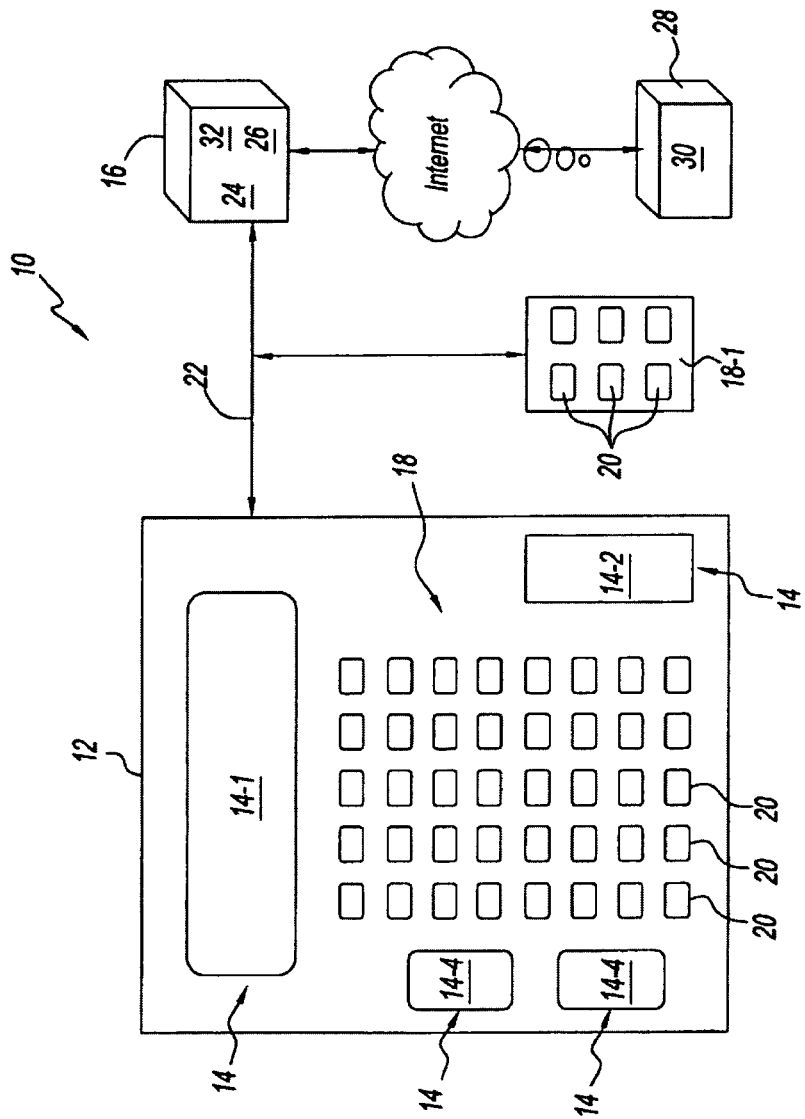
FIG. 1 is a schematic view illustrating an exemplary embodiment of a medical product dispensing system according to the present disclosure.

Referring to the drawings and in particular to FIG. 1, an exemplary embodiment of a medical product dispensing system 10 is shown. Advantageously, system 10 is configured to dispense medical products having restricted distribution requirements without the need for interaction between the purchaser/user/consumer (hereinafter purchaser) and a licensed practitioner or other sales associate.

It should be understood that the purchaser of the medical product may be the same as or different from the user of the medical product. For example, it is contemplated by the present disclosure for a parent or other guardian to purchase the medical product for a child or other dependant. However, and for purposes of clarity, the present disclosure shall be described by way of example only having the purchaser and user being one and the same. Thus, the user of system 10, the user of the medical product, and the purchaser are, for purposes of clarity, described herein being one and the same.

System 10 provides an effective guide to the purchaser through a series of medical history and medical product related questions, and also provides product specific information of interest and importance to the purchaser.

Thus, system 10 provides an electronic device to replace a learned intermediary (i.e., licensed practitioner) by capturing the critical elements that a learned intermediary provides, and also provides effective collateral methods for the safe and effective use of a prescription or restricted access medical product in an over the counter environment.

More particularly, system 10 provides an interactive computer controlled vending machine having access to a purchaser recognition system, a product specific self-selection algorithm 24 and, in some embodiments, a product specific de-selection algorithm 26 for any medical product. The system 10 dispenses the medical product selected by a purchaser if the purchaser qualifies for the medical product. In the instance where the medical product has restrictions for distribution based on the product's labeling or governmental agency specifications, system 10, as determined by the self-selection algorithm 24 in accordance with information inputted by the purchaser, determines whether the purchaser qualifies for the medical product. Upon subsequent requests for the particular medical product, the system 10 can dispense a subsequent sales unit of the particular medical product if the purchaser remains qualified for the medical product as determined by the de-selection algorithm 26 in accordance with the prior and new information inputted by the purchaser, or limitations as specified by the label or other governmental agencies.

In an exemplary embodiment of the present disclosure, system 10 includes a vending machine 12 having one or more person-machine-interface devices 14. System 10 also includes a controller 16 in communication with vending machine 12 and interface devices 14. Vending machine 12 defines a storage space 18 configured to receive one or more different medical products 20 therein.

Figure 2:
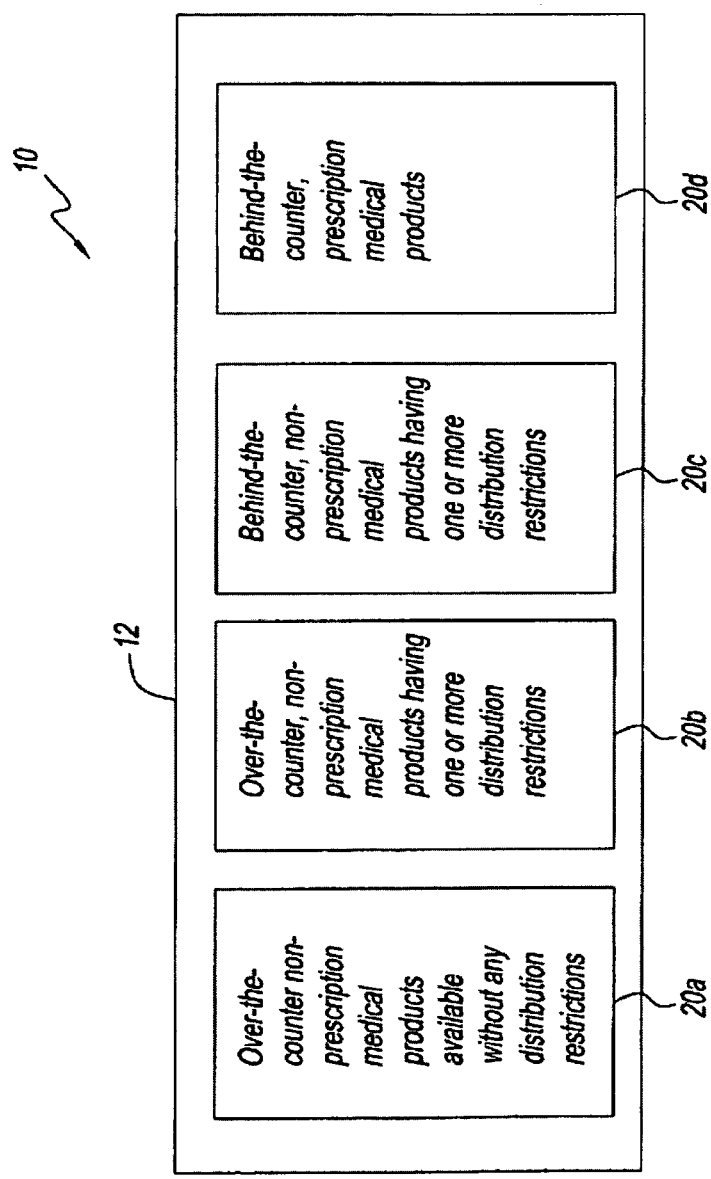
FIG. 2 illustrates the various classes of medical products that are contemplated for use with the dispensing system of FIG. 1.

FIG. 2 illustrates the various categories of medical products 20 that are contemplated for use with the dispensing system of FIG. 1. For example, system 10 can be used to distribute certain over-the-counter, non-prescription medical products 20a that can be sold without any distribution restrictions imposed by a regulating body (e.g., FDA, DEA) or other relevant competent regulating authority. Here, system 10 may distribute medical products 20a without the need for algorithms 24, 26. For example, medical products 20a can include those products that have restricted access due to theft or shrinkage. Further, it is contemplated by the present disclosure for a retail company and/or product manufacturer to place restrictions on the use of one or more medical products 20a that differ (e.g., may be more stringent) from those required by the aforementioned regulating bodies/authorities. In these instances, the retailer and/or manufacturer may opt to use algorithms 24, 26 in the distribution of various medical products 20a.

In addition, system 10 can be used to distribute other medical products 20b, 20c, and 20d that have one or more distribution restrictions.

Thus, system 10 can be used to distribute certain over-the-counter, non-prescription medical products 20b (e.g., PSE containing products and the like) that can be only be sold upon verification of one or more attributes, such as age of the purchaser. It is also contemplated by the present disclosure for system 10 to be updated to include other over-the-counter, non-prescription medical products 20b that may be later changed to restricted sales.

System 10 distributes medical products 20b without the need for de-selection algorithm 26, but rather uses a selection algorithm 24 that requires only birth date or age verification and, in some instances, a number of purchases of the particular medical product 20b within a predetermine period of time.

In this embodiment, system 10 can be configured to store or save purchase data on controller 16. Since controller 16 is, in some embodiments, common to multiple retail locations, system 10 is configured to automatically monitor store-to-store purchases of restricted medical products 20b (e.g., PSE containing products). In this manner, system 10 can prevent the sale of such restricted medical products based on allowed purchase quantities even though the purchaser's information (i.e., age) meets the necessary limits.

System 10 can be used to facilitate, or provide the collateral methods to allow for the distribution of certain behind-the-counter, non-prescription medical products 20c, such as the aforementioned dual status medicines, medicines classified as Schedule 4 and Schedule 3 in Australia, and pharmacy sales in the United Kingdom.

Also, system 10 can be used to facilitate, or provide the collateral methods to allow for the distribution of certain behind-the-counter, prescription medical products 20d that meet or can be made to meet the requirements for being "switched" from prescription to non-prescription status. Further, system 10 can be used to facilitate, or provide the collateral methods to allow for the distribution of certain behind-the-counter, non-prescription medical products 20c that meet or can be made to meet the requirements for being "switched" from behind-the-counter to an over-the-counter status.

During the distribution of medical products 20c, 20d, system 10 provides, via algorithms 24, 26, an interactive collateral measures compliance device that, for example, ensures compliance to the labeling requirements and thus, ensures the confidence necessary for switching the medical products from prescription to non-prescription status and/or from behind-the-counter status to over-the-counter status.

Accordingly, as used herein the term "distribution restricted medical products" includes one or more of products 20b, 20c, and 20d.

Referring again to FIG. 1, interface device 14 can be any type of data entry and communication device 14-1 such as, but not limited, to visual display screen, a standard alphanumeric key board, a mouse or pointing device, a touch screen, a credit card reader, a bar code reader, a speaker, a microphone, a voice recognition device, a printer, a wired communication port, a wireless communication port, and any combinations thereof. In this manner, a purchaser using vending machine 12 can input personal information, if required, such as name, address, medical insurance information, age and past medical history, current over the counter or prescription medication information, payment information, and other information requested by controller 16 and used by algorithms 24, 26 to determine whether to dispense medical product 20 to the purchaser.

When vending machine 12 is not in use, system 10 controls data entry and communication device 14-1 via controller 16 to provide verbal and/or visual health information and/or advertising to people in the vicinity of the vending machine. Data entry and communication device 14-1 can be physically incorporated into vending machine 12 or can be in electrical communication with the vending machine In other embodiments, and as will be discussed in more detail herein below, interface device 14 can also include one or more identification devices 14-2, one or more biometric data devices 14-3, one or more payment devices 14-4 (only one shown), and any combinations thereof.

In its simplest form, the identity of the purchaser can be accomplished by the purchaser manually entering in their identity information via data entry and communication device 14-1. In other embodiments or supplemental to this embodiment, system 10 can include identification device 14-2 that is any device commonly used to electronically verify the identity of particular purchaser. For example, identification device 14-2 can be a magnetic stripe reader or bar code reader that accepts information from an identification card such as a driver's license, medical insurance or medical history and medical diagnostic card should such technology be developed, credit card, and others. In other embodiments, identification device 14-2 can include more complex a identification device such as, but is not limited to, a finger print scanner, a retinal scanners, a facial recognition device, a DNA scanner, and any combinations thereof.

Biometric data collection device 14-3 is integral to vending machine 12 and is configured to measure one or more biometric characteristics of the purchaser for use by system 10 in the self-selection algorithm 24 and, when necessary, the de-selection algorithm 26. For example, biometric data collection device 14-3 can be a device such as, but not limited to, a blood pressure monitor or a blood glucose monitor such that system 10 can collect a blood pressure reading or glucose reading from the device.

As used herein, the terms "biometric data" and "biometric characteristics" are used interchangeably and shall collectively mean measured data representative of one or more physiological conditions of the purchaser. Such "biometric data" and "biometric characteristics" can be measured via contact directly with the purchaser via for example, a blood pressure cuff, a thermometer, an infrared blood gas analyzer, and the like. The "biometric data" and "biometric characteristics" can also be measured via samples taken from the purchaser such as height, weight, whole blood, serum, saliva, urine, feces and any combinations thereof. Furthermore, the "biometric data" and "biometric characteristics" can include any clinically measurable values normally obtained by a licensed medical practitioner via a physical exam or ordered as part of formal laboratory analysis.

It should be recognized that the present disclosure illustrates biometric data collection device 14-3 by way of example only as collecting blood pressure and blood glucose data. Of course, it is contemplated by the present disclosure for biometric data collection device 14-3 to collect any purchaser biometric data such as, but not limited to, purchaser body temperature, blood sugar, the level of the low density lipoprotein (LDL) form of cholesterol, the level of the high density lipoprotein (HDL) form of cholesterol, the total cholesterol level, triglyceride level, blood oxygen saturation rates, heart rate, blood pressure, body temperature, lung function indices (i.e., forced expiratory volume) or any other pulmonary, cardiovascular, blood, urine and stool chemistry analysis information available to a licensed healthcare practitioner.

It should also be recognized that vending machine 12 is not limited to entry of biometric data only via biometric data collection device 14-3. Rather, it is contemplated by the present disclosure for vending machine 12 to allow collection of biometric data in a plurality of ways of which collection device 14-3 allows for measurement directly at the vending machine.

In some embodiments, the purchaser can input biometric data via data entry and communication device 14-1. For example, the purchaser could type in a blood pressure or cholesterol reading into vending machine 12 via data entry device 14-1. Alternately, the purchaser could present a diagnosis card 30 or medical history card to the data entry device 14-1 for the data entry device to scan or read the information on the card, including biometric data, if any, into the vending machine.

Alternately, the purchaser could place a purchaser supplied biometric measurement device (not shown) in electrical communication with vending machine 12 via data entry and communication device 14-1 in examples where the data entry device is a communication port. In this manner, a purchaser could connect a purchaser provided device, such as a blood glucose monitoring device, to vending machine 12 and download or communicate one or more data points to system 10.

In still other embodiments, the purchaser can input biometric data via data entry and communication device 14-1 by using the data entry device to authorize controller 16 to obtain the biometric data from an external test or laboratory site 28. For example, prior to interfacing with vending machine 12, the purchaser could submit themselves to one or more testing protocols at external test site 28. The results of these testing protocols being stored on a database 30 associated with the external test or laboratory site 28. Here, the purchaser can authorize vending machine 12 to access the results available on database 30 via a network connection such as the Internet.

Payment device 14-4, if desired, can accept one or more types of payment. For example, payment device 14-4 can be a credit card reader or a debit card reader, can be a cash or coin accepting device, and any combinations thereof. In some embodiments, vending machine 12 can determine via controller 16 the purchaser's cost for medical product 20 based on insurance provider information entered by the purchaser.

Vending machine 12 and/or controller 16 can be configured to control storage space 18 to store medical product 20 at an ambient storage condition, a conditioned storage condition, or any combinations thereof. As used herein, the ambient storage condition shall mean that medical product 20 is exposed to an amount of light, a storage temperature, and a storage humidity within space 18 that is ambient to the location where machine 12 resides. In contrast, the conditioned storage condition shall mean that space 18 is controlled to meet a recommended storage condition for medical product 20 by controlling or conditioning one or more of an amount of light, a storage temperature, a storage humidity, and any combinations thereof.

It is further contemplated for vending machine 12 to include a plurality of storage spaces 18, where some spaces are controlled to ambient storage conditions acceptable for medical product 20 therein, while other spaces provide controlled storage conditions acceptable for medical product 20 therein.

In this manner, vending machine 12 can be configured, as needed, to store any desired medical product 20 within space or spaces 18.

It should be recognized that vending machine 12 is described above by way of example as defining one or more storage spaces 18 therein. However, it is contemplated by the present disclosure for storage spaces 18 to be an auxiliary storage device 18-1 that is physically attached to or otherwise controlled by vending machine 12 and/or controller 16. For example, it is contemplated by the present disclosure for storage spaces 18 to be defined in a drawer-like drug supply cabinet such as those commercially available in the hospital setting.

Medical product 20 can be stored or packaged in a selected sales unit appropriate for the particular medicine and condition being treated. In some instances, the selected sales unit size may be subject to FDA or other governmental agency requirement. For example, medical product 20 can be stored in a sales unit having a thirty-day supply of the medical product.

In one embodiment, vending machine 12 includes one or more sensors (not shown) in communication with controller 16. In this manner, system 10 can monitor the internal inventory of medical product 20 within spaces 18 and communicate to a vendor or retailer when refill is needed.

In the illustrated embodiment of system 10, controller 16 is shown being remote from vending machine 12 and communicating with one another via a network 22. However, it is also contemplated by the present disclosure for controller 16 to be resident in vending machine 12. Moreover, it is contemplated for system 10 to include two controllers, one resident in vending machine 12 and one remote from the vending machine, where the two controllers communicate over network 22. Network 22 can be any desired communication network such as, but not limited to, a wide-area-network, the Internet, and others.

System 10 includes self-selection algorithm 24 and, in some embodiments, de-selection algorithm 26 resident on controller 16. In one embodiment, controller 16 and, hence algorithms 24, 26, reside in a central location in electrical communication with a plurality of vending machines 12. In other embodiments, controller 16 and, hence algorithms 24, 26, are resident on one vending machine 12. Here, algorithms 24, 26 are automatically updated from a remote central location, as desired.

In use of system 10, a purchaser requests the purchase of a particular medical product 20 stored within vending machine 12 via input device 14. In response to the purchase request, controller 16 can control vending machine 12 to request the purchaser to enter particular general personal information specific to the purchaser such as, but not limited to, name, age, address, social security number, past medical history, current medications, past use of the particular medical product, and the like. Of course, it is contemplated by the present disclosure for vending machine to not require any personal information be entered by the purchaser.

Based on the particular medical product 20 being requested and, when required, the general personal information, controller 16 determines whether the purchase request is a first or initial request for the particular medical product 20 by the purchaser. In other embodiments where no personal information is available, controller 16 can ask the purchaser whether the purchase request is a first or initial request or a second or subsequent request for the particular medical product 20 by the purchaser. If the request is an initial request, controller 16 executes self-selection algorithm 24. However, if the request is not an initial request, but rather is a second or subsequent request, the controller 16 executes de-selection algorithm 26.

Broadly speaking, self-selection algorithm 24 determines if the purchaser is eligible for use of medical product 20, while de-selection algorithm 26 determines if the purchaser remains eligible for the medical product.

As used herein, the term "self-selection" is the process of a purchaser using a product specific algorithm that reflects those critical concerns and information identified by the governmental agency and included in the product's label, and then help or guide the purchaser on whether or not to select or use a particular product based on information listed on the product label taking into account his/her personal medical history, demographics and signs and symptoms of the condition to be treated. The self-selection process provides a risk-benefit analysis at the time of initial purchase so that the benefit of starting treatment is weighed against the risks associated with not starting treatment or seeking a physician's advice.

As used, herein the term "de-selection" is the process where the purchaser, who has already started therapy with a particular product, has again reviewed the critical elements and information (e.g., warnings, cautions, directions) of the approved label as well as their current medical history to make a determination of whether use of the product should be continued or discontinued. The de-selection process may also contain the same or different questions of critical interest that were listed in the self-selection process. The de-selection process provides a risk-benefit analysis each time the purchaser attempts to re-purchase a particular product so that the benefit of continuing treatment is weighed against the risks associated with continuing treatment. Further, de-selection process can automatically limit the length of therapy to a predetermined length by for example monitoring how many purchase requests for the particular medical product have been made by the particular user.

Selection algorithm 24 is configured to pose a plurality of questions to the purchaser via data entry and communication device 14-1 based on the approved labeling of the purchaser's desired medical product 20. In some instances, the plurality of questions can include purchaser acknowledgement of specific warnings or other critical information. The purchaser's answers to the questions are entered via devices 14-1, 14-2, and 14-3, as required. In response, to the purchaser's answers, selection algorithm 24 determines whether the purchaser is eligible for the particular medical product 20 requested.

De-selection algorithm 26 is also configured to pose a plurality of questions to the purchaser via data entry and communication device 14-1 based on the purchaser's desired medical product 20 and past use of the system 10. Again, in some instances, the plurality of questions can include purchaser acknowledgement of specific warnings or other critical information. The purchaser's answers to the questions are entered via devices 14-1, 14-2, and 14-3, as required. In response, to the purchaser's answers, selection algorithm 24 determines whether the purchaser is eligible for continued use of the particular medical product 20 requested.

Thus, system 10 restricts access to medical product 20 when the purchaser's information and past use of the system 10 for the same medication or device, as determined by algorithms 24, 26, does not comply with the necessary conditions, labeling or restrictions for the selected medical product. For example, incorrect answers to questions provided by algorithms 24, 26 results in controller 16 preventing vending machine 12 from dispensing medical product 20.

System 10 provides a patient driven system, located at the point-of-sale, that establishes the patient identification, accepts first and subsequent purchase requests for a particular medical product 20, uses algorithms 24, 26 to determine if that patient is eligible to receive or continue to receive that medical product, provides warning and heeding information to the purchaser about the medication via data entry and communication device 14-1 in verbal, display and/or printed form, reviews and calculates any limitation or compliance requirements as indicated in the approved labeling or set by governmental agencies, and completes the sales transaction via payment device 14-4, if desired, and dispenses the medical product when appropriate.

Advantageously, system 10 provides accuracy and compliance to the selection criteria within algorithms 24, 26, and approved labeling, provides significant consumer education before and during use, provides full retail access to medical products 20 having restricted distribution status (i.e., products 20b, 20c, and 20d), handles the sales transaction at the vending machine 12, verifies that the medical condition still exists when subsequent purchases are requested, documents and saves patient information, accesses information and provide a reason for denial or need to be referred to a Doctor, documents and saves sales information (e.g., PSE) without the need for a pharmacist or other retail employee. Thus, system 10 can be used for FDA/DEA/State mandated restricted medical products (e.g., PSE containing products, dual status medicines, and the like), as well as for worldwide behind-the-counter drug restrictions models.

In this manner, system 10 can be used to transfer a non-prescription, behind-the counter medical product to a general sales medical product without the need of the intervention of licensed health care practitioners. System 10 can be used as an approved risk management tool and a collateral method to allow for the switch of a prescription medical product to a non-prescription, over-the-counter or general sales medical product. Further, system 10 can be used as an approved risk management tool and a collateral method to allow for the switch of a non-prescription, behind-the-counter medical product to an over-the-counter or general sales medical product.

In the event that system 10 determines, via self-selection or de-selection algorithms 24, 26, that the purchaser is not qualified to receive the particular medical product 20 selected, the system controls vending machine 12 to not dispense the medical product 20. In some embodiments, system 10 can provide instructions, directions, and/or advice to the purchaser, via data entry and communication device 14-1, regarding the steps necessary to obtain the particular medical product. For example, system 10 can provide a written instruction, a visual instruction, a verbal instruction, and any combinations thereof (via data entry and communication device 14-1).

Figure 3:
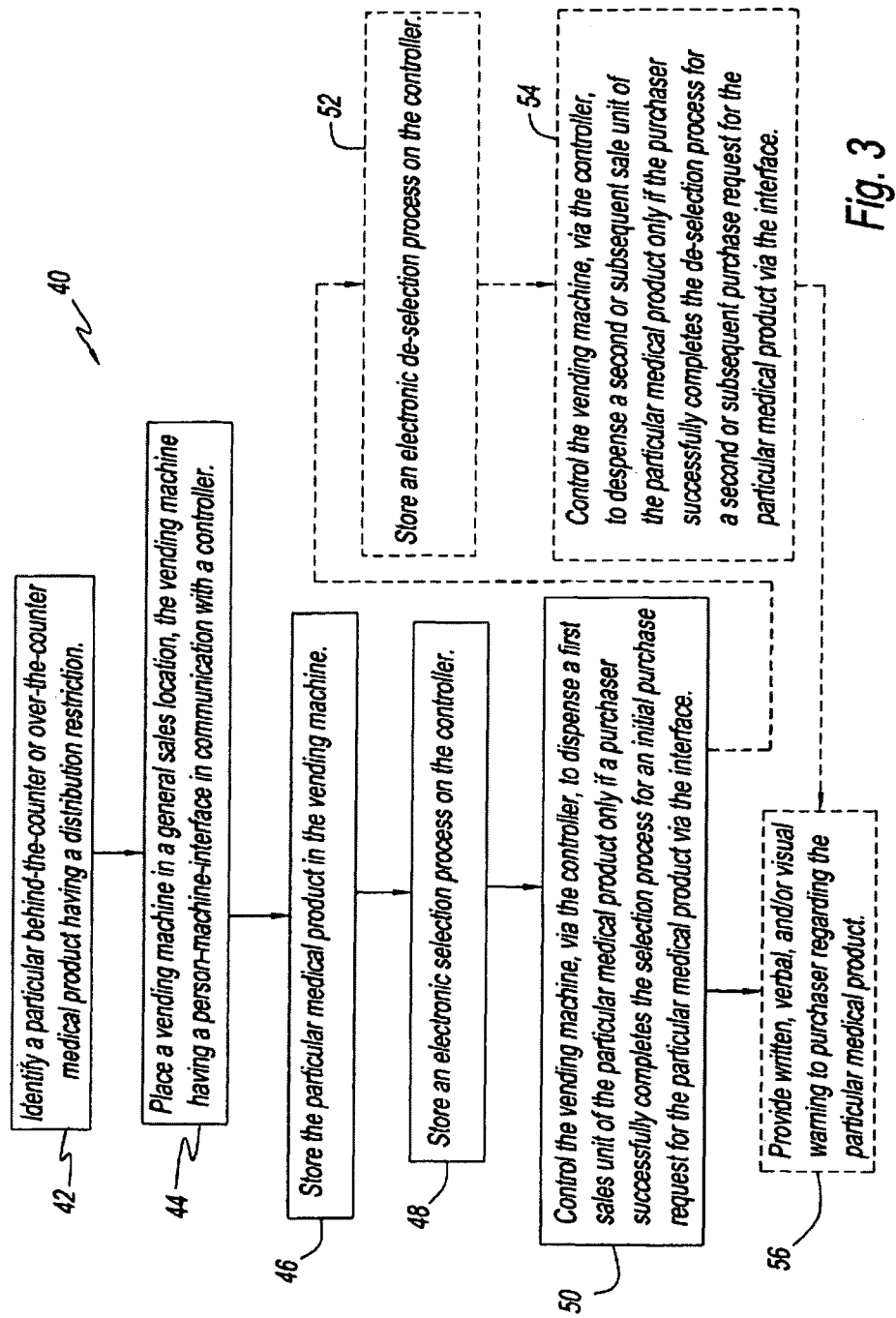
FIG. 3 illustrates a method for dispensing medical products according to an exemplary embodiment of the present disclosure.

Referring now to FIG. 3, a method for transferring non-prescription, behind-the-counter or over-the-counter medical product having distribution restrictions to a general sales medical product is illustrated generally by reference numeral 40.

Method 40 identifies a particular behind-the-counter or over-the-counter medical product that has one or more distribution restrictions (20b, 20c) to be transferred at step 42 and places a vending machine 12 in a general sales location at step 44. As discussed above with respect to FIG. 1, vending machine 12 has interface device 14 in communication with a controller 16.

Method 40 includes storing a supply of the medical product in the vending machine at step 46 and storing an electronic selection process 24 on the controller 16 at step 48. Next, method 40 controls the vending machine, via the controller, to dispense a first sales unit of the particular medical product only if a purchaser is identified and successfully completes the self-selection process based on either the approved labeling requirements or other governmental restriction regarding an initial purchase request for the medical product via the interface device 14 at step 50.

In some embodiments, method 40 further includes storing an electronic de-selection process 26 on the controller 16 at step 52. Finally, method 40 controls the vending machine, via the controller, to dispense a second or subsequent sales unit of the particular medical product only if a purchaser successfully completes the de-selection process and meets the approved labeling requirements or other governmental restriction regarding for a second or subsequent purchase request for the particular medical product via the interface device 14 at step 54.

In other embodiments, method 40 can include a warning step 56 before or after dispensing step 50 or 54. Here, method 40 can provide a warning, caution, and/or instruction (herein after "information") to the purchaser via data entry and communication device 14-1 regarding the use of the particular medical product. For example, method 40 can control data entry and communication device 14-1 at step 56 to provide written information, visual information, verbal information, and any combinations thereof.

It is contemplated by the present disclosure for method 40, at step 56, to customize the information to the particular purchaser using the biometric data and/or one or more of the purchaser's answers.

Figure 4:
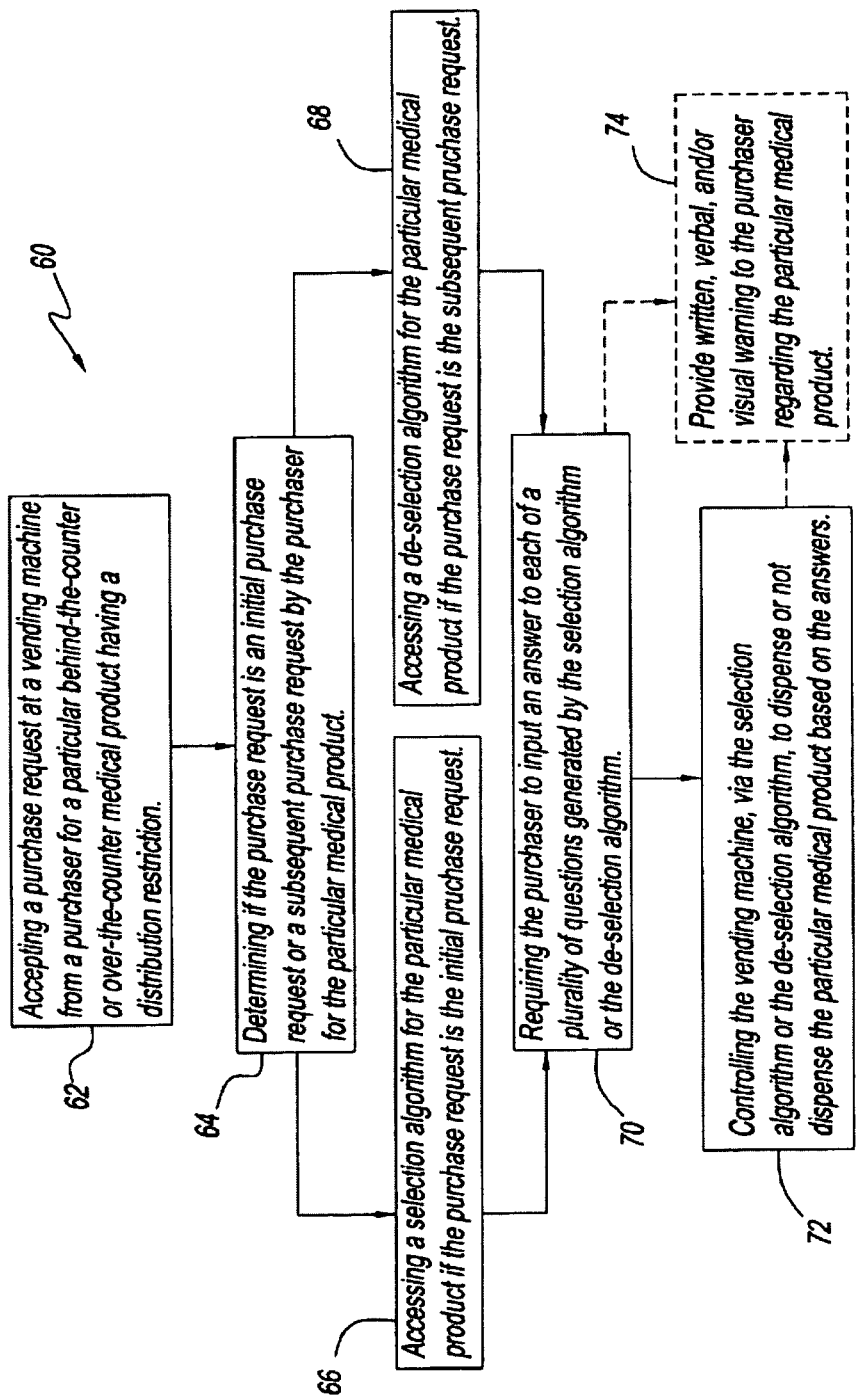
FIG. 4 illustrates an alternate exemplary embodiment of a method for dispensing medical products according to the present disclosure.

Referring now to FIG. 4, an alternate exemplary embodiment of a method for transferring non-prescription, behind-the counter medical products to general sales medical products is illustrated generally by reference numeral 60.

Method 60 includes a step 62 where a purchase request from a purchaser of the vending machine 12 for a particular non-prescription, behind-the-counter medical product 20 is accepted. Once accepted, method 60 includes a determining step 64, where the method determines if the purchase request is an initial purchase request or a subsequent purchase request by the purchaser for the particular medical product. Method 60 then accesses a selection algorithm if the purchase request is the initial purchase request at step 66 or a de-selection algorithm if the purchase request is the subsequent purchase request at step 68.

After accessing the appropriate algorithm, method 60 requires the purchaser to input an answer to each of a plurality of questions and reviews information generated by the selection algorithm or the de-selection algorithm at step 70. Next, method 60 controls the vending machine, via the selection algorithm or the de-selection algorithm, to dispense or not dispense the particular medical product based the answers at step 72.

In other embodiments, method 60 can include a warning and caution step 74 before or after steps 70 or 72. Here, method 60 can provide a warning, caution, and/or instruction (herein after "information") to the purchaser via data entry and communication device 14-1 regarding the use of the particular medical product. For example, method 60 can control data entry and communication device 14-1 at step 74 to provide written information, visual information, verbal information, and any combinations thereof.

It is also contemplated by the present disclosure for method 60, at step 74, to customize the information to the particular purchaser using the biometric data and/or one or more of the purchaser's answers.

It is also contemplated by the present disclosure for warning step 74 to include the potential follow-up with the purchaser by a licensed practitioner or other practitioner regarding the purchase of the medical product if so indicated by the label.

For example, system 10 can provide contact data from the purchaser to a manufacturer of the medical product or to the owner of the system 10. In this manner, the purchaser can be contacted in a follow-up manner, namely a predetermined period of time after the purchase, to provide any critical information regarding the safe and effective use of the product, and determine whether the purchaser has any questions or should have any follow-up regarding the use of the medical product. Advantageously, system 10 can provide the data necessary for the follow-up in a manner that complies with the requirements of the Health Insurance Portability and Accountability Act (HIPAA).

In another example, system 10 can communicate a follow-up reminder directly to the purchaser. In some embodiments, system 10 can send an e-mail message, an electronic phone message, a text message, a mailed letter directly to the purchaser reminding the purchaser to, for example, verify their blood pressure is below a predetermined limit or to see their physician if the signs and symptoms of the condition being treated become worse.

Figure 5:
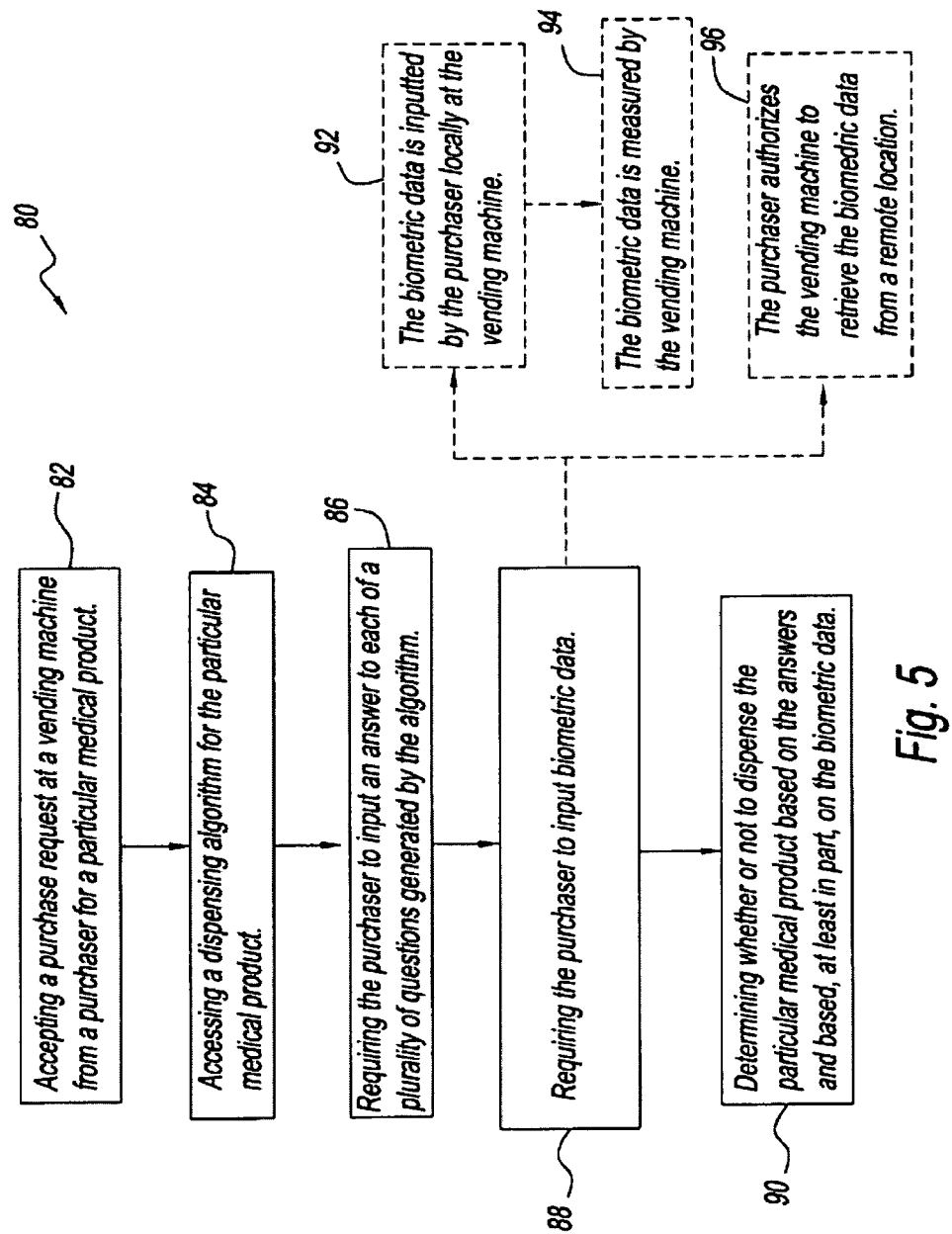
FIG. 5 illustrates another alternate exemplary embodiment of a method for dispensing medical products according to the present disclosure.

Referring now to FIG. 5, an exemplary embodiment of a method of dispensing medical products is illustrated generally by reference numeral 80.

Method 80 includes a step 82 where a purchase request from a purchaser of the vending machine 12 for a particular medical product 20 is accepted. Once accepted, method 80 then accesses a dispensing algorithm for the particular medical product at step 84.

After accessing the appropriate algorithm, method 80 requires the purchaser to input an answer to each of a plurality of questions and see information generated by the algorithm at step 86. Next, method 80 requires a purchaser to input biometric data at step 88. Next, method 80 determines whether to dispense or not dispense the particular medical product based on the answers and at least in part on the biometric data at step 90.

It is also contemplated by the present disclosure for method 80, at step 90, to use the biometric data and/or the purchaser's answers to customize the purchase of the medical product for the purchaser. For example, method 80, at step 90, can use the biometric data (e.g., weight) and/or one or more of the purchaser's answers (e.g., age) to customize one or more attributes of the purchase. The attributes of the purchase that can be customized by method 80 based on the answers and at least in part on the biometric data at step 90 can include a dosage of the medical product, a use instruction for the user, a warning, and others.

Thus, method 80 can not only determine whether or not to dispense the particular medical product based on the answers and at least in part on the biometric data at step 90, but also to customize one or more attributes of the purchase.

In some embodiments, the biometric data of step 88 can be inputted locally at the vending machine 12 at step 92. For example, the locally inputted data at step 92 can be inputted to system 10 via communication device 14-1 or by connecting a purchaser supplied biometric measurement device (not shown) to vending machine 12 via data entry and communication device 14-1 as discussed above with respect to FIG. 1. Also, the locally inputted data at step 92 by measuring at step 94 the biometric data directly at vending machine 12 via biometric data collection device 14-3 as discussed above with respect to FIG. 1.

In other embodiments, the purchaser can authorize at step 96 vending machine 12 to obtain the biometric data from an external test site 28 as discussed above with respect to FIG. 1.

The systems and methods according to the present disclosure, by eliminating the need to interact with a pharmacist or learned health care intermediate, allow the dispensing of non-prescription, behind-the-counter medical products in locations previously impossible.

Moreover, it has been determined by the present disclosure that the systems and methods according to the present disclosure advantageously allow medical products having a prescription status, to be switched, in some instances, to over-the-counter, non-prescription status and/or for medical products having a behind-the-counter status, to be switched to an over-the-counter status.

Medical products that the FDA has already approved for prescription use can be "switched" to non-prescription use when it has been determined to the satisfaction of the FDA that, among other factors, the medical product is safe for use under the conditions suggested in the proposed labeling. Such "switch" applications generally require data from actual use and labeling comprehension studies to demonstrate that the product can be safely and effectively used without the supervision of a practitioner licensed by law to administer or use the product. System 10 advantageously provides an interactive collateral measures and compliance device that, for example, ensures compliance to the labeling requirements and thus, enhances the confidence associated with switching medical product from prescription to non-prescription status.

Advantageously, the systems and methods of the present disclosure provide a risk management and collateral methods model that easily and effectively addresses the issues with label comprehension, label compliance, and chronic use.

Figure 6:
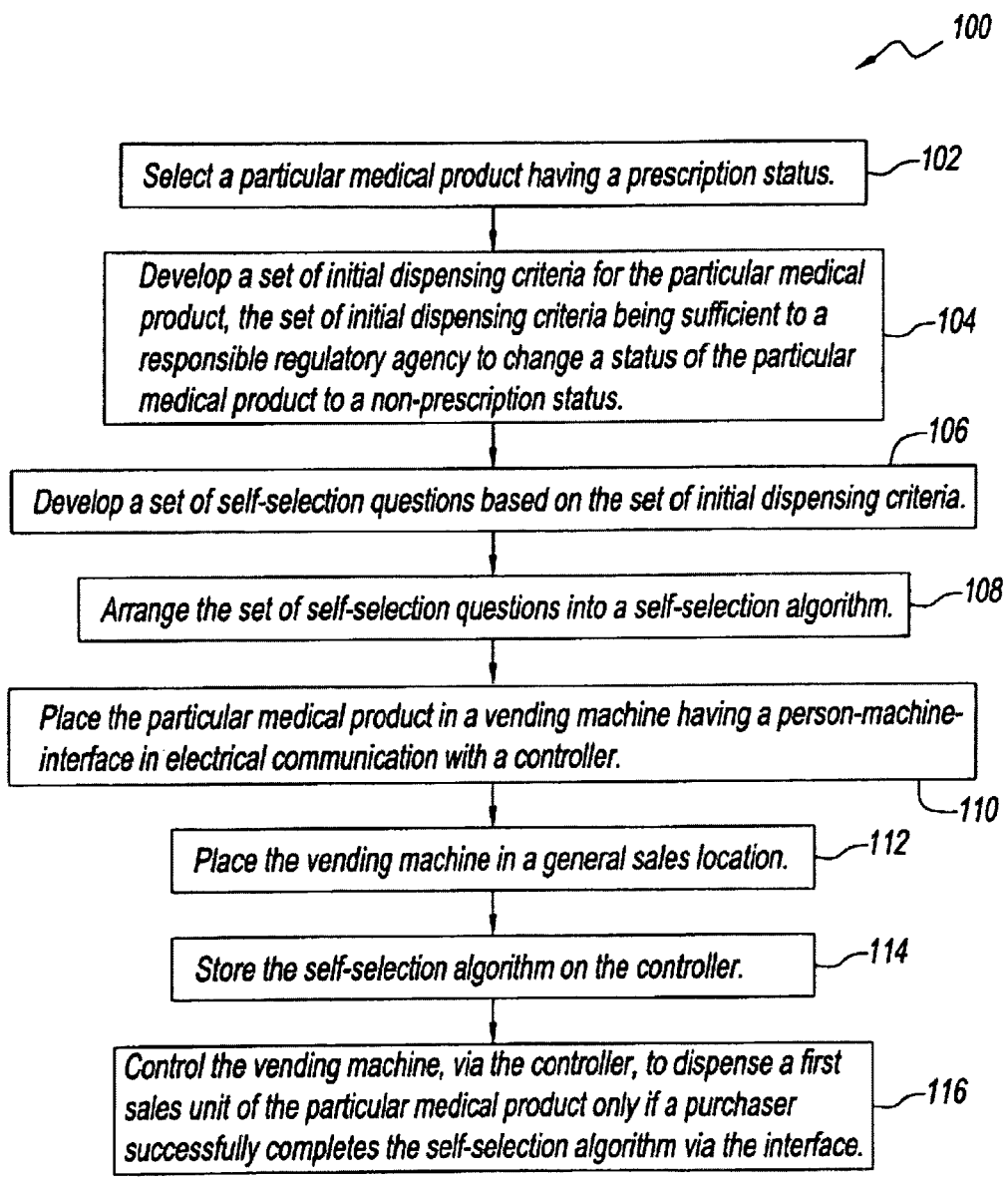
FIG. 6 illustrates an exemplary embodiment of a method for switching a behind-the-counter, prescription medical products to an over-the-counter, non-prescription medical product using a vending machine according to the present disclosure.

An exemplary embodiment of a method of switching a prescription medical product to a non-prescription, over-the-counter medical product according to the present disclosure is illustrated in FIG. 6 and generally referred to by reference numeral 100.

Method 100 includes a medicine selection step 102, where a particular medical product having a prescription status is selected to be switched to a non-prescription, over-the-counter status.

Once selected, method 100 includes a first developing step 104, where a set of initial dispensing criteria a developed. The set of initial dispensing criteria for the particular medical product includes criteria sufficient to a responsible regulatory agency, such as the FDA, to authorize changing the status of the medical product to the non-prescription status. Next, method 100 includes a second developing step 106, where a set of selection questions based on the set of initial dispensing criteria are developed.

Method 100 arranges the set of selection questions, during an arranging step 108, into a selection algorithm. Method 100 then includes a first placing step 110 where the medical product is placed in a vending machine and a second placing step 112 where the vending machine is placed in a general sales location. Method 100 stores the selection algorithm on the controller at step 114. Finally, method 100, during a dispensing step 116, controls the vending machine, via a controller, to dispense a first sales unit of the particular medical product only if a purchaser successfully completes the selection algorithm via the interface device 14.

In some embodiments, the purchaser may desire a second or subsequent sales unit of the medical product. Here, method 100 can include provisions for maintaining or allowing the medical product with the non-prescription status for second or subsequent purchases by the same purchaser.

Figure 7:
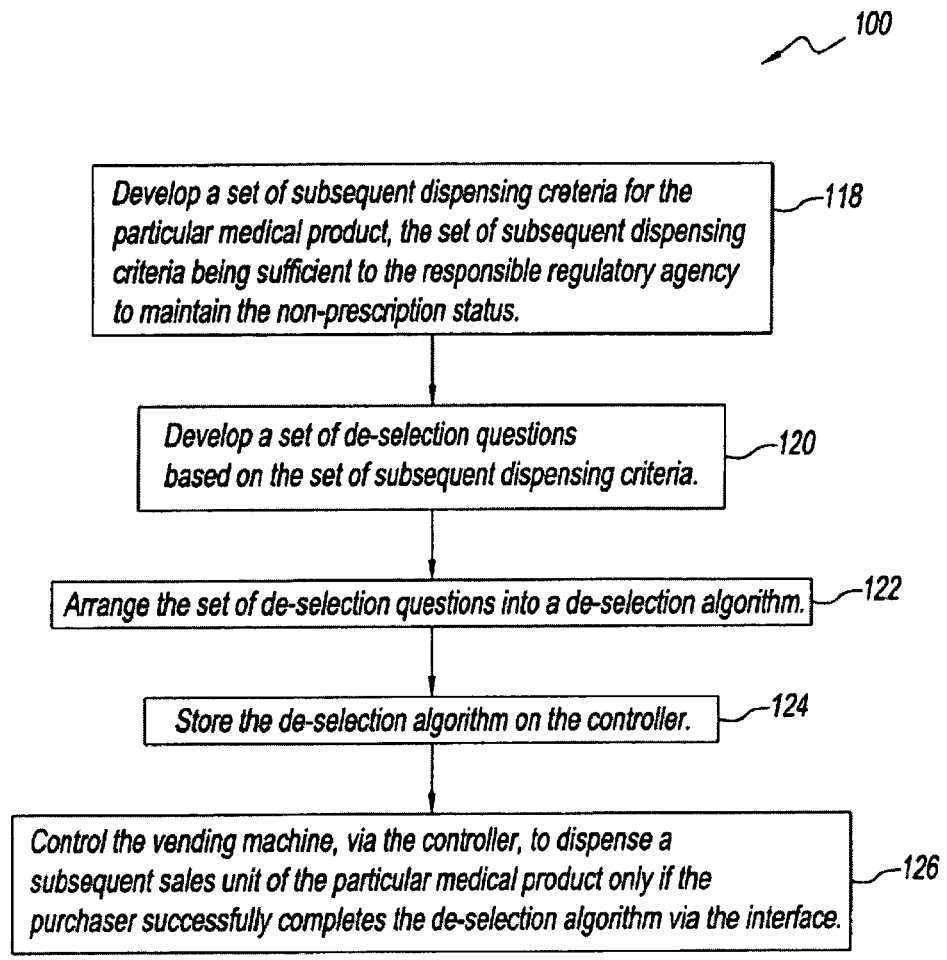
FIG. 7 illustrates an alternate exemplary embodiment of the method of FIG. 6.

In this embodiment illustrated in FIG. 7, method 100 further includes a third developing step 118, where a set of subsequent dispensing criteria are developed. The set of subsequent dispensing criteria for the particular medical product includes criteria sufficient to the responsible regulatory agency or authority, such as the FDA, to allow and or maintain the status of the medical product at the non-prescription status. Next, method 100 includes a fourth developing step 120, where a set of de-selection questions based on the set of subsequent dispensing criteria are developed.

Method 100 arranges the set of de-selection questions, during a second arranging step 122, into a de-selection algorithm. Method 100 stores the de-selection algorithm on the controller at step 124. Finally, method 100, during a subsequent dispensing step 126, controls the vending machine, via the controller, to dispense a second or subsequent sales unit of the particular medical product only if a purchaser successfully completes the de-selection algorithm via the interface device 14.

In this manner, method 100 can advantageously facilitate switching prescription medical products to non-prescription status in a way that ensures the criteria for obtaining the first and subsequent doses of the medical product are in compliance with the approved labeling by preventing dispensing of the medical product in the event certain selection or de-selection criteria are not met.

It should be recognized that method 100 is described above by way of example only in use switching a medical product 20d having a prescription status to a medical product 20a having a non-prescription, over-the-counter status. Of course, it is contemplated by the present disclosure for method 100 to find equal use in switching a medical product 20c having a non-prescription, behind-the-counter status to a medical product 20a having a non-prescription, over-the-counter status.

Referring now to FIG. 8, an exemplary embodiment of a method 150 for the use of system 10 having selection and de-selection algorithms 24, 26 is shown.

Figure 8A:
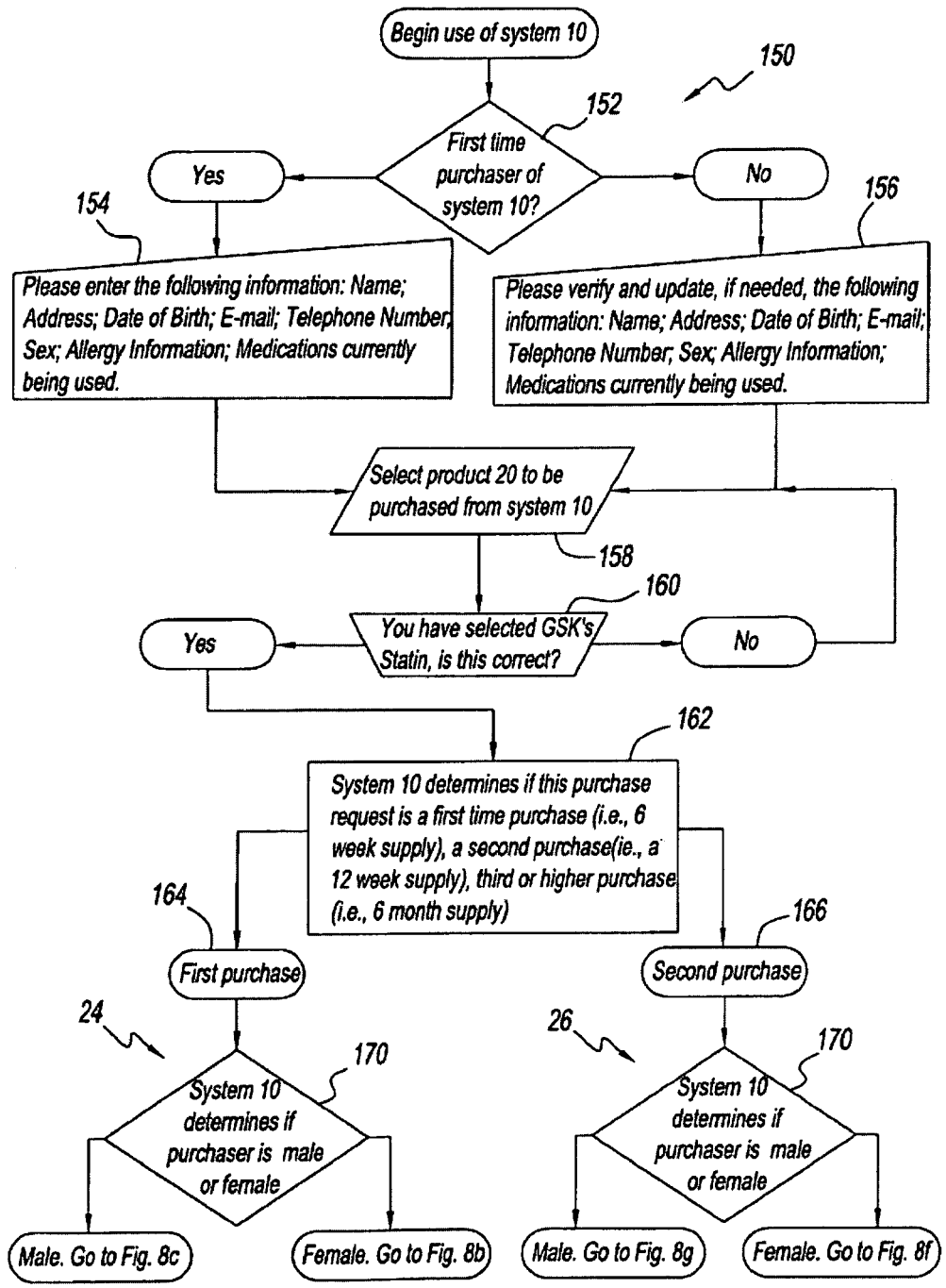
FIG. 8($a$) through FIG. 8($g$) illustrate an exemplary embodiment of a self-selection algorithm and a de-selection algorithm.

Upon beginning the use of system 10 as shown in FIG. 8a, method 150 can determine whether or not the purchaser is a first time purchaser at step 152. If the purchaser is a first time purchaser, then method 150, at step 154, can, in some embodiments, require the purchaser to enter personal identification information such as, but not limited to name, address, date of birth, e-mail address, telephone number, sex, allergy information, medications currently being used, and others. In this embodiment, if the purchaser is a repeat purchaser, then method 150, at step 156, requires the purchaser to enter enough information to allow the system to access the purchaser's records stored on system 10. Once retrieved, method 150 requires the purchaser to verify and update previously entered enter personal identification information.

In other embodiments, system 10 may not required identification of the purchaser via entry of personal information. Here, method 150 progresses directly to step 158 discussed below.

Next, the purchaser selects the desired medical product 20 to be purchased at step 158 and requires the purchaser to verify the selection at step 160. Upon verification of the desired product 20, method 150 retrieves self-selection algorithm 24 and de-selection algorithm 26 for the desired medical product 20.

In the illustrated example where the desired medical product 20 is a cholesterol lowering medicine such as those available in the "statin" class of drugs, which are commercially available from the assignee of the present application, method 150 determines, at step 162, whether the purchase request by the particular purchaser for that particular product 20 is a first purchase request 164 or a second request 166. It should be recognized that in other examples of algorithms 24, 26 for other medical products, method 150 may only need to differentiate first purchases from second purchases, while still other algorithms 24, 26 for other medical products may require method 150 to differentiate each purchase from another When method 150 determines that the purchase request is the first purchase request 164, system 150 utilizes self-selection algorithm 24 for the particular medical product 20 selected. In the illustrated example, system 150 utilizes self-selection algorithm 24 for the medical product.

Conversely, when method 150 determines that the purchase request is the second purchase request 166, system 150 utilizes a de-selection algorithm 26 for the particular medical product 20 selected, namely the medical product.

The self-selection and de-selection algorithms 24, 26 determine, based on information entered/verified during steps 154, 156, whether the purchaser is a male or a female at step 170. Based on the results of determination step 170, method 150 continues to utilize the correct portion of self-selection and de-selection algorithms 24, 26, respectively.

Figure 8B:
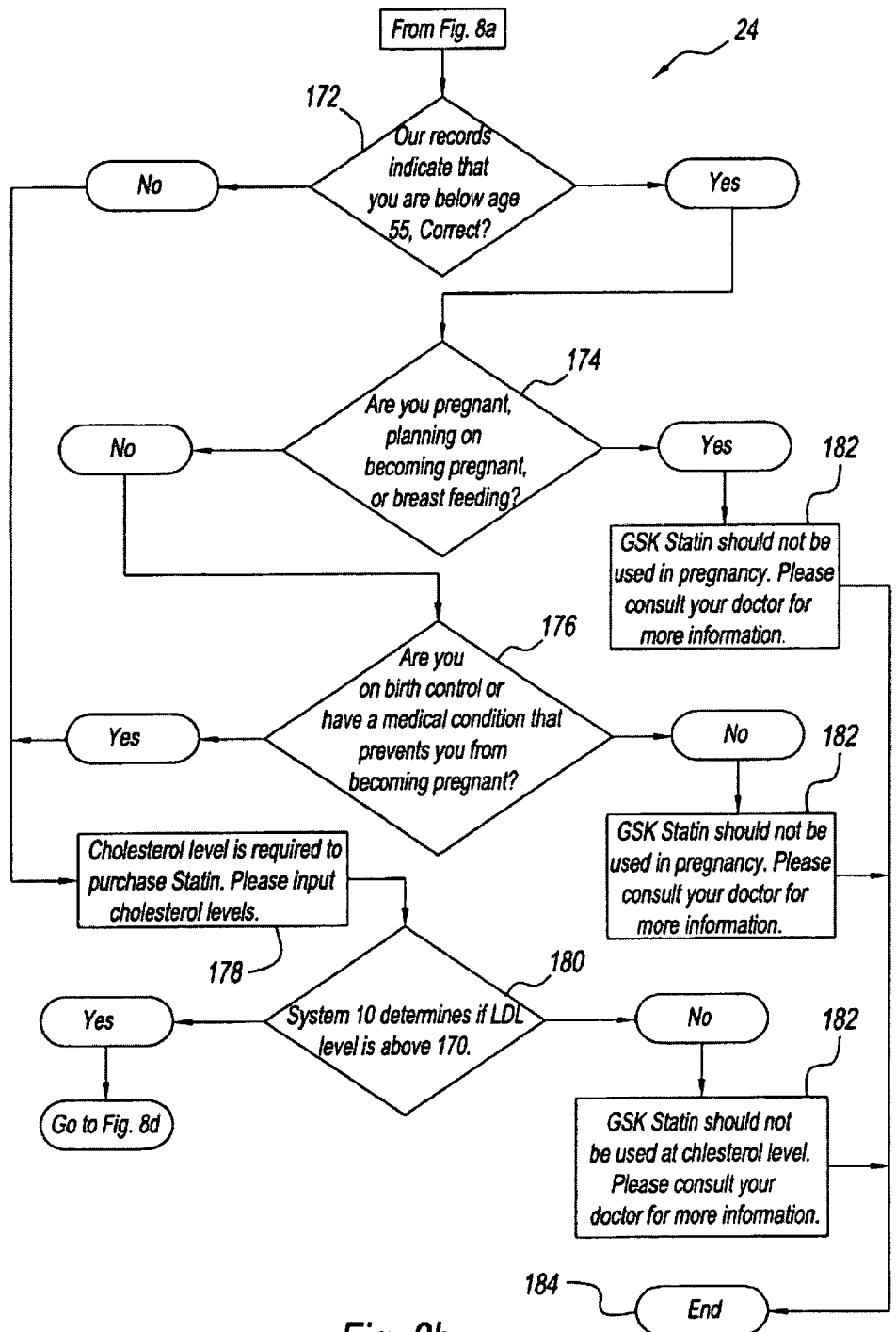

When method 150 determines at step 170 (FIG. 8a) that the purchaser is a first time purchaser of the particular medical product 20 and is female, method 150 continues to utilize the self-selection algorithm 24 as show in FIG. 8b. Referring now to FIG. 8b, method 150, based on information entered/verified during steps 154, 156, determines whether the female purchaser is below the age of 55 and verifies this age with the purchaser at step 172. If the purchaser is below the age of 55, namely is within the child bearing years, method 150 determines whether the purchaser is pregnant at step 174, and if not, whether the purchaser is incapable of becoming pregnant at step 176.

When method 150 determines at steps 172 (via age) and steps 174/176 that the female purchaser is not pregnant, the method requires the purchaser to input their cholesterol level at step 178. The cholesterol level can be inputted at step 178 manually using data entry device 14-1, by connecting a user supplied cholesterol measuring device to system 10, by measuring the level directly at system 10, or any other method discussed herein above.

After receiving the purchaser's cholesterol level, method 150, via self-selection algorithm 24, compares this level to a predetermined therapy level at step 180. For example, if the purchaser's cholesterol level is above the predetermined therapy level shown as above 170 milligrams per deciliter (mg/dL), then method 150 continues to utilize the self-selection algorithm 24 as show in FIG. 8d.

However, if method 150 determines at any of steps 174, 176, or 180 that the medical product 20 is not appropriate for the purchaser, the method notifies the purchaser of this status at step 182 and terminates the purchase request at step 184.

Figure 8C:
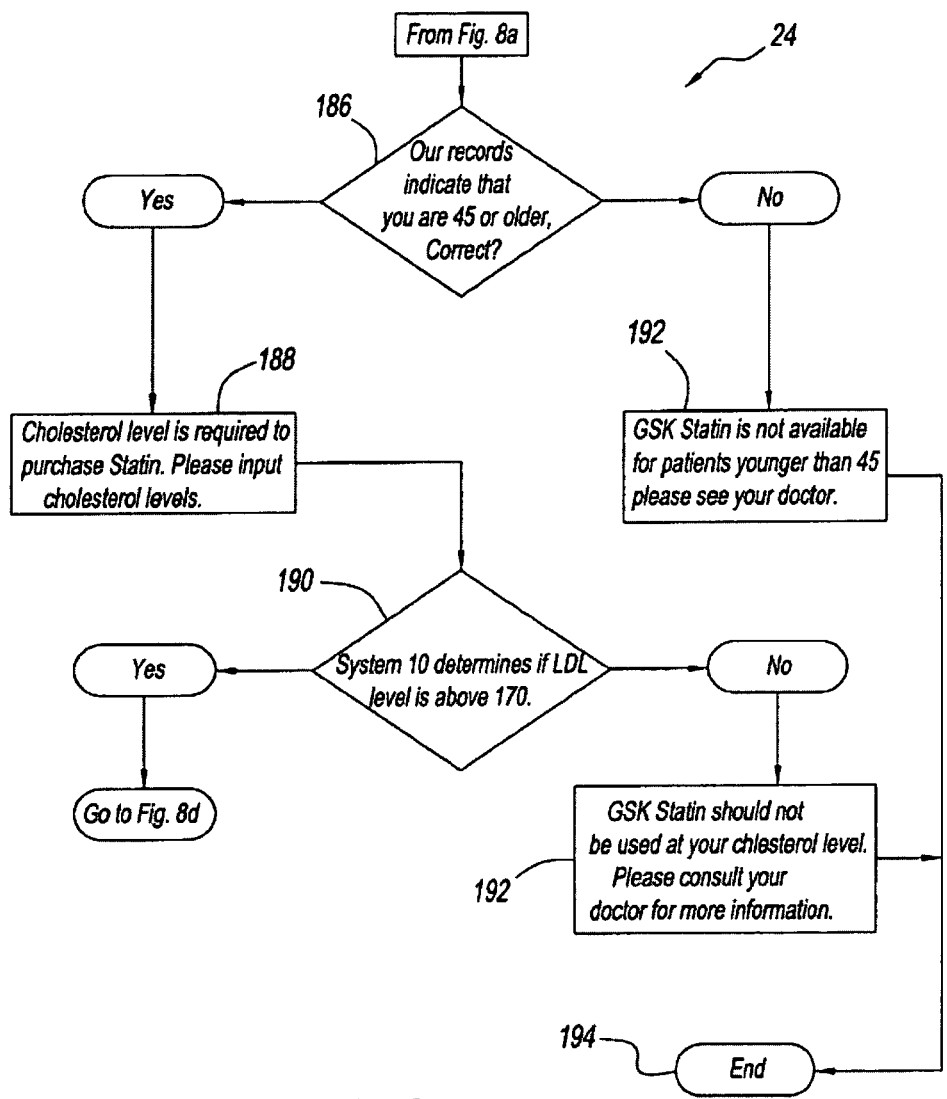

When method 150 determines at step 170 (FIG. 8a) that the purchaser is a first time purchaser of the particular medical product 20 and is male, method 150 continues to utilize the self-selection algorithm 24 as show in FIG. 8c. Referring now to FIG. 8c, method 150, based on information entered/verified during steps 154, 156, determines whether the male purchaser is 45 years old or older and verifies this age with the purchaser at step 186.

When method 150 determines at step 186 that the male purchaser is within the appropriate age bracket (i.e., 45 or older), the method requires the purchaser to input their cholesterol level at step 188. Again, the cholesterol level can be inputted at step 178 by any method discussed herein above. After receiving the purchaser's cholesterol level, method 150, via self-selection algorithm 24, compares this level to a predetermined therapy level at step 190. For example, if the purchaser's cholesterol level is above the predetermined therapy level shown as above 170 mg/dL, then method 150 continues to utilize the self-selection algorithm 24 as shown in FIG. 8d.

However, if method 150 determines at either of steps 186 or 190 that the medical product 20 is not appropriate for the purchaser, the method notifies the purchaser of this status at step 192 and terminates the purchase request at step 194.

Figure 8D:
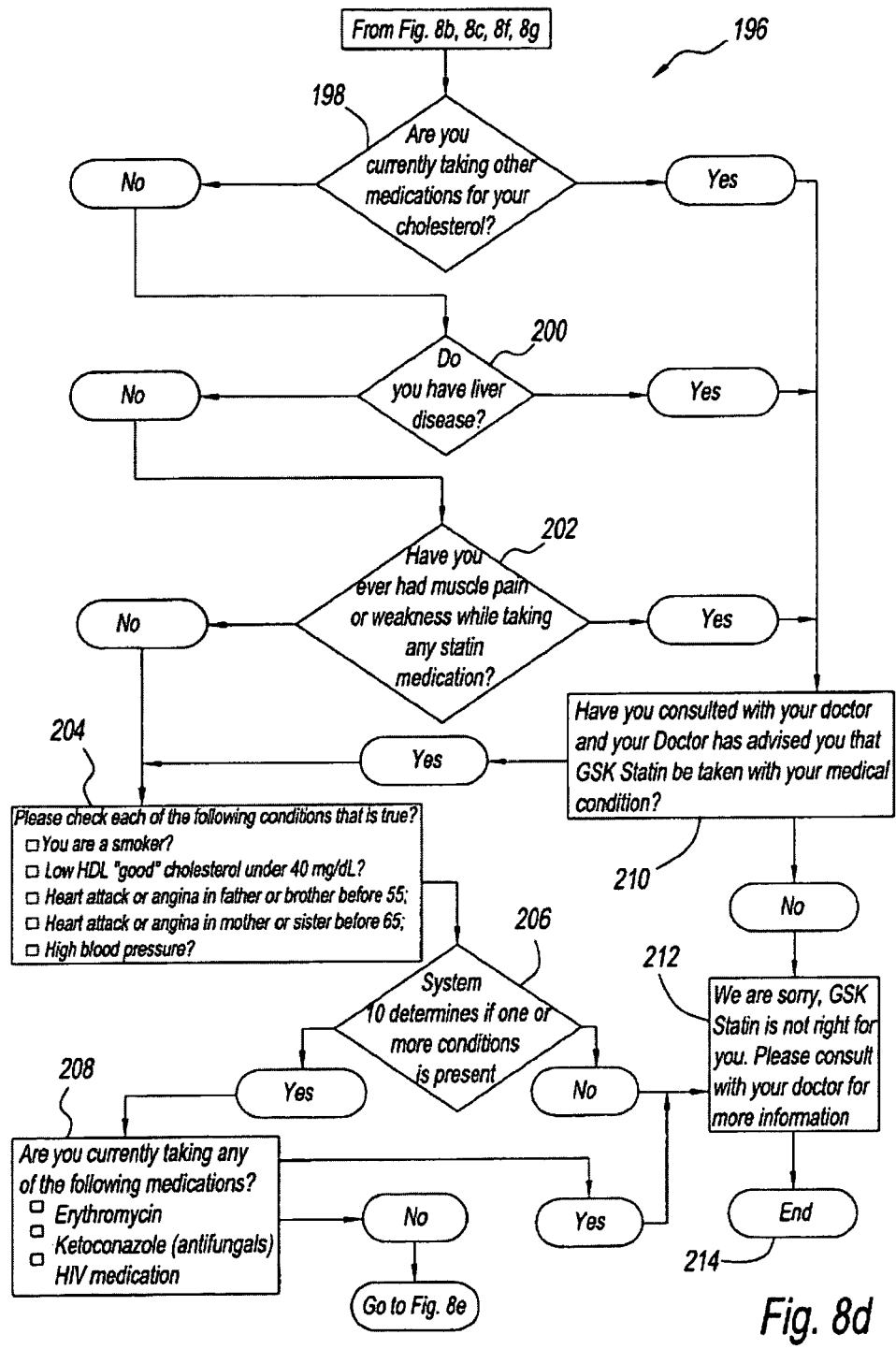

When method 150 preliminarily determines that a particular purchaser is appropriate for the selected medical product 20 at step 180 (FIG. 8b) or step 190 (FIG. 8c), the method continues to utilize self-selection criteria 24 to complete the analysis of the appropriateness of statin therapy for the purchaser as shown in FIG. 8d using a plurality of risk factors 196.

Referring now to FIG. 8d, method 150 determines at step 198 whether the purchaser is using any other cholesterol medications. Method 150 further determines whether the purchaser has liver disease at step 200 or has had a prior adverse reaction to any statin medications at step 202.

If method 150 determines via steps 198, 200, 202, that the purchaser remains eligible for statin medication, then the method requests information related to particular risk factors with the purchaser at step 204 and then determines whether the number of risk factors identified at step 204 exceed a predetermined risk level at step 206. If purchaser remains eligible for statin medication after step 206, method 150 determines if the purchaser is taking a medication that interacts with statin medication at step 208. If, after completion of step 208, the purchaser remains eligible for statin medication, method 150 proceeds to a dispensing step 216 shown in FIG. 8e.

Figure 8E:
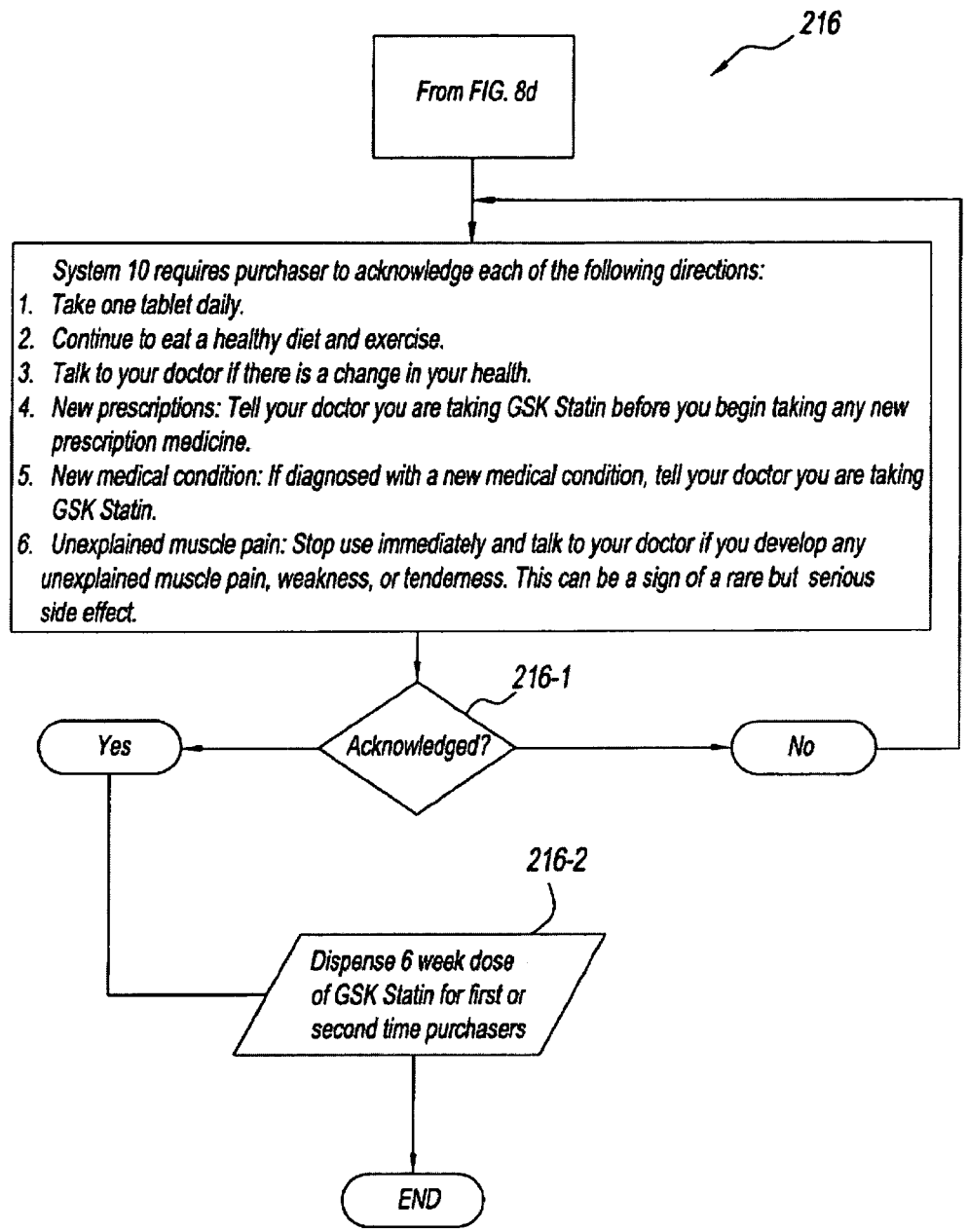

Referring to FIG. 8e, method 150, during dispensing step 216, requires the purchaser to acknowledge a plurality of warnings and instructions with respect to the medical product 20. Method 150 verifies at step 216-1 that each is acknowledged, and if so, dispenses the appropriate amount of the medical product 20 at step 216-2.

If method 150 determines via steps 198, 200, 202, that the purchaser is preliminarily ineligible for statin medication, the method determines if purchaser discussed this situation with their doctor and received approval none-the-less at step 210. If step 210 determines approval was provided, method 150 continues to step 206. However, if step 210 determines approval was not provided, method 150 informs the purchaser that medical product 20 is not appropriate for them at step 212 and terminates the purchase request at step 214.

Figure 8F:
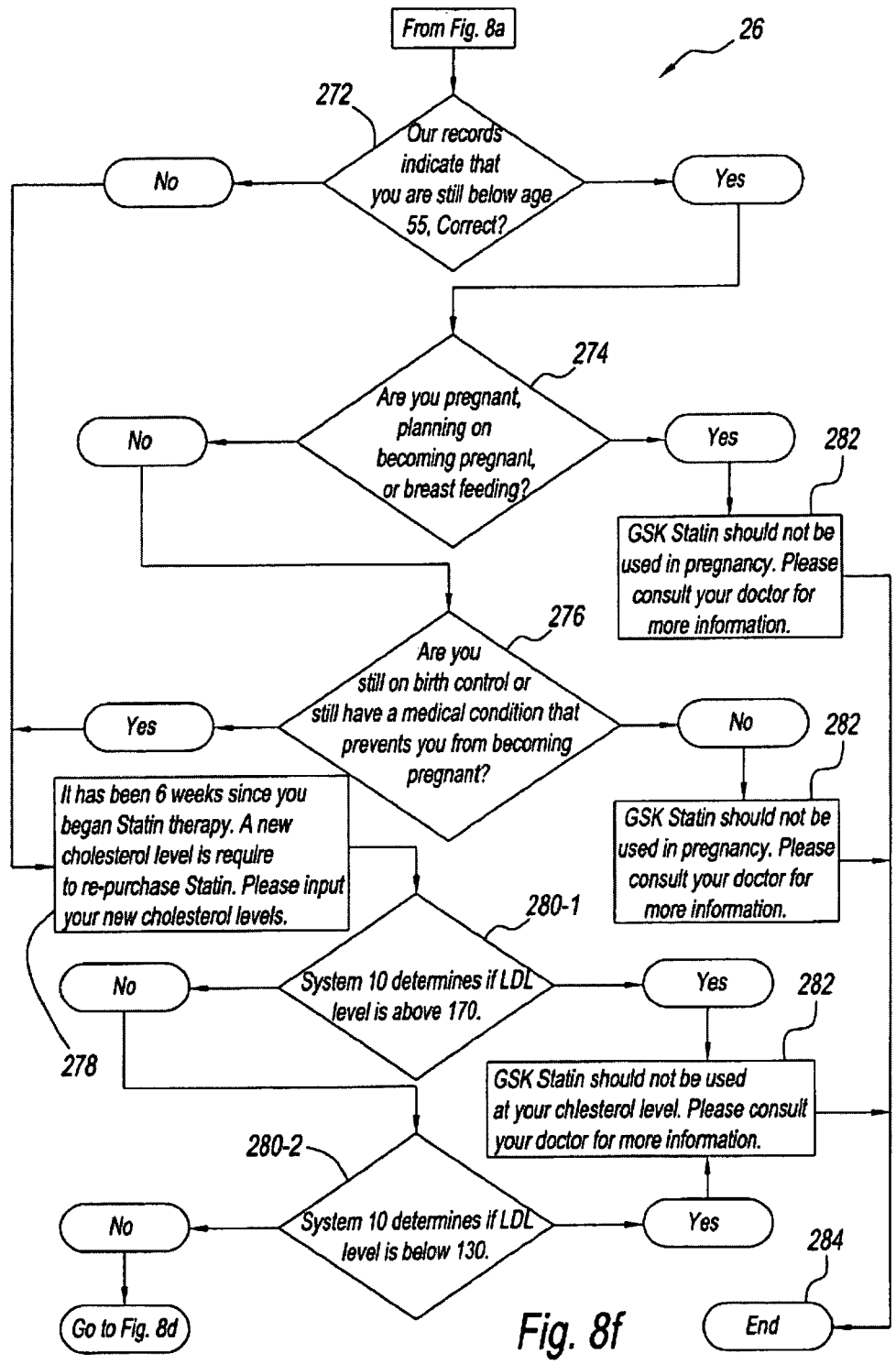

Returning for a moment to FIG. 8a, when method 150 determines at step 170 that the purchaser is a second time purchaser of the particular medical product 20 and is female, method 150 continues to utilize the de-selection algorithm 26 as shown in FIG. 8f. Referring now to FIG. 8f, method 150, based on information verified during steps 156, determines whether the female purchaser is still below the age of 55 and verifies this age with the purchaser at step 272. If the purchaser is below the age of 55, namely is within the child bearing years, method 150 determines whether the purchaser is pregnant at step 274, and if not, whether the purchaser is incapable of becoming pregnant at step 276.

When method 150 determines at steps 272 (via age) and steps 274/276 that the female purchaser is not pregnant, the method requires the purchaser to input their new cholesterol level at step 278, taken since the beginning of therapy with statin medication. The cholesterol level can be inputted at step 278 by any method discussed herein above.

After receiving the purchaser's cholesterol level, method 150, via de-selection algorithm 26, compares this level to a maximum predetermined therapy level at step 280-1 and a minimum predetermined therapy level at step 280-2. For example, if the purchaser's cholesterol level is within the therapy level of 130 mg/dL to 170 mg/dL, then method 150 continues to utilize the de-selection algorithm 26 as show in FIG. 8d and discussed above.

However, if method 150 determines at any of steps 274, 276, 280-1, or 280-2 that the medical product 20 is not appropriate for the purchaser, the method notifies the purchaser of this status at step 282 and terminates the purchase request at step 284.

Figure 8G:
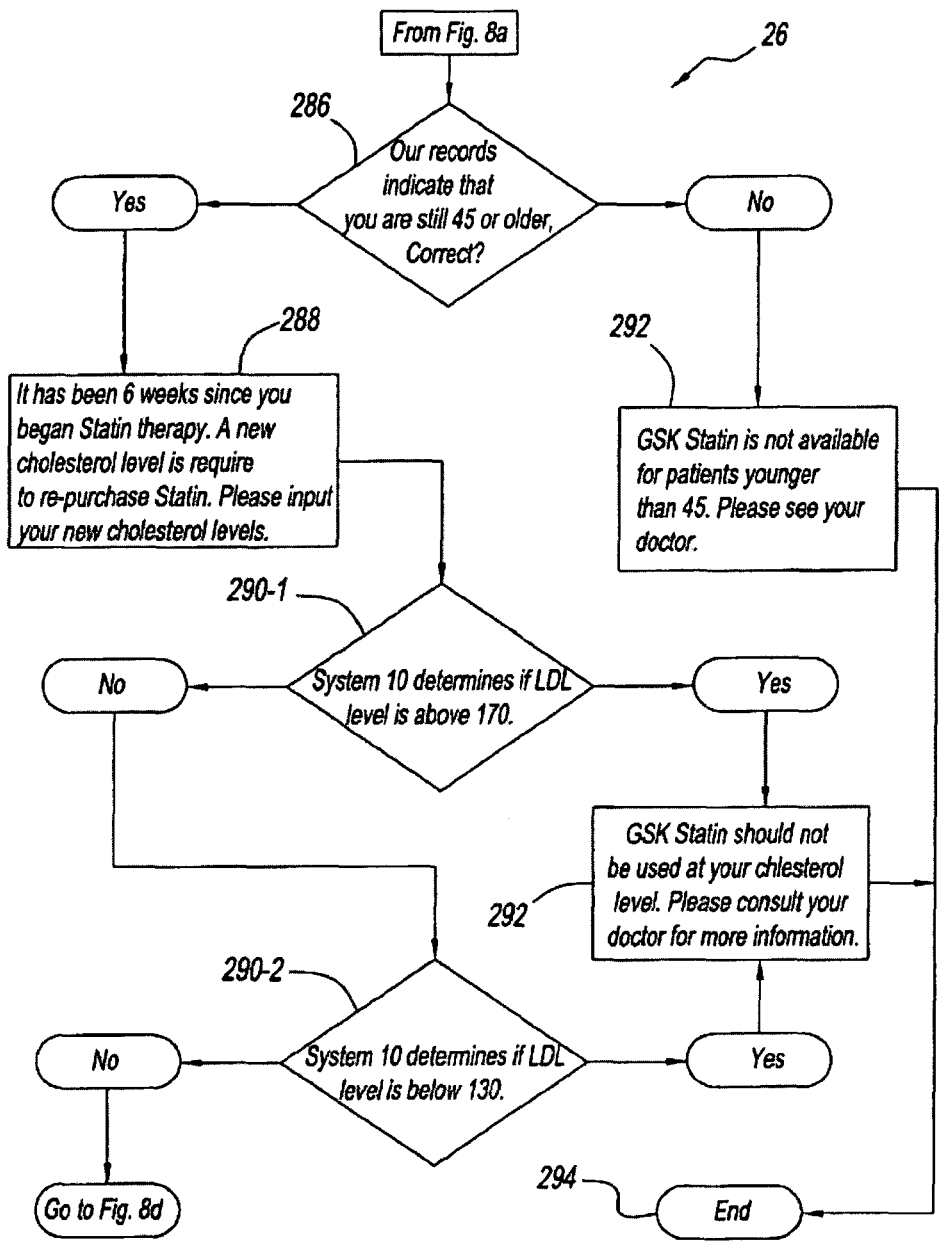

When method 150 determines at step 170 (FIG. 8a) that the purchaser is a second time purchaser of the particular medical product 20 and is male, method 150 continues to utilize the de-selection algorithm 26 as show in FIG. 8g. Referring now to FIG. 8g, method 150, based on information verified during step 156, determines whether the male purchaser is 45 years or older and verifies this age with the purchaser at step 286.

When method 150 determines at step 286 that the male purchaser is within the appropriate age bracket, the method requires the purchaser to input their new cholesterol level at step 288, taken since the beginning of therapy with statin medication. The cholesterol level can be inputted at step 288 by any method discussed herein above.

After receiving the purchaser's cholesterol level, method 150, via de-selection algorithm 26, compares this level to a maximum predetermined therapy level at step 290-1 and a minimum predetermined therapy level at step 290-2. For example, if the purchaser's cholesterol level is within the therapy level of 130 mg/dL to 170 mg/dL, then method 150 continues to utilize the de-selection algorithm 26 as shown in FIG. 8d.

However, if method 150 determines at either of steps 286, 290-1, or 290-2 that the medical product 20 is not appropriate for the purchaser, the method notifies the purchaser of this status at step 292 and terminates the purchase request at step 294.

When method 150 preliminarily determines that a particular purchaser is appropriate for the selected medical product 20 at step 280-2 (FIG. 8f) or step 290-2 (FIG. 8g), the method continues to utilize de-selection algorithm 26 to complete the analysis of the appropriateness of statin therapy for the purchaser as shown in FIG. 8d using the plurality of risk factors 196.

In some embodiments, de-selection algorithm 26 determines whether the purchaser has been taking the medical product in a prescribed dosage. For example, as a result of successful purchase of completion of self-selection algorithm 24, system 10 may provide an amount of medical product 20 that should last a predetermined period of time. Based on the date of the subsequent attempt to purchase the same medical product 20, de-selection algorithm 26 can determine if the purchaser has not taken the medication in the desired manner. Thus, system 10 can determine if the purchaser has returned for a subsequent purchase of the medical product too soon, which may indicate taking too much of the medical product. Alternately, system 10 can determine if the purchaser has returned for a subsequent purchase of the medical product too late, which may indicate taking not enough of the medical product.

Accordingly, and in this manner, system 10 can provide for interactive compliance to the collateral measures necessary to meet the requirements set forth by the FDA for switching such prescription medicines and/or transferring restricted distribution status medical products to general sales products.

In addition, system 10 can be configured to assist the purchaser in matching an appropriate medical product 20 to symptoms or states of a disease currently being experienced by the purchaser. For example, and referring again to FIG. 1, controller 16 can include a matching algorithm 32 resident thereon.

Matching algorithm 32 is configured to provide exemplary symptoms or disease-states to the purchaser via data entry and communication device 14-1 in a visual or auditory form. As used herein a "visual form" shall mean that the exemplary symptom or disease-state is provided to the purchaser in non-textual form such as, but not limited to, a picture. In this manner, matching algorithm 32 allows the purchaser to match their particular symptom or disease-state to the exemplary symptom or disease-state presented. Once the purchaser identifies their symptom or disease-state via matching algorithm 32, controller 16 provides the purchaser with a list via device 14-1 of one or more medical products 20 within vending machine 12 that are appropriate for that symptom or disease-state.

Take for example a purchaser who has a cough and desires to purchase a non-prescription, over-the-counter cough medicine. System 10 determines if the purchaser desires assistance, via matching algorithm 32, in selecting the appropriate medical product for their cough. Once selected, matching algorithm 32 can present a plurality of different auditory cough examples to the purchaser via data entry and communication device 14-1.

In this example, system 10 can ask the purchaser if their cough sounds like a loose or productive cough, and then play a sample loose cough recording from a speaker 14-1 on vending machine 12. If the loose cough sample is not selected, then system 10 can ask the purchaser if their cough sounds like a dry or non-productive cough, and then play a sample dry cough recording from the speaker 14-1.

Matching algorithm 32 can continue to present exemplary symptoms or disease-states to the purchaser until the purchaser identifies one that matches their particular condition. Upon selection of a particular symptom or disease-state via matching algorithm 32, system 10 can provide the purchaser with optional products 20 within vending machine 12 that are appropriate for such symptoms or disease-states.

In some embodiments, matching algorithm 32 can only present those medical products 20 that do not have adverse interactions with medical products currently being used by the purchaser or medical conditions (e.g., high blood pressure) experienced by the purchaser.

However, matching algorithm 32 can also prompt the user to see a medical professional or doctor in the event that no matching symptom or disease-state is selected, in the event that no medical product 20 is available to the purchaser due to other factors (e.g., age, sex, potential for drug interaction, and warnings such as allergy, etc), and any combinations thereof.

It should be recognized that matching algorithm 32 is described above by way of example using auditory symptom or disease-state matching. Of course, it is also contemplated by the present disclosure for matching algorithm 32 to provide visual symptom or disease-state matching such as, for example, providing non-textual visual examples of a condition such as, but not limited to, a skin rash that requires treatment.

It should also be recognized that matching algorithm 32 is described above by way of example in use with medical products 20a without distribution restrictions. However, it is contemplated by the present disclosure for matching algorithm 32 to find use with any medical product 20, namely those without any distribution restrictions (i.e., products 20a) and those with distribution restrictions (i.e., products 20b, 20c, 20d).

In some embodiments, it is contemplated by the present disclosure for system 10 to be configured for distribution of one particular medical product. Here, system 10 can have matching algorithm 32 for only that particular medical product. In use, the purchaser would use system 10 for the particular medical product they are interested in purchasing by approaching the system advertised for that particular medical product. Then, controller 16 resident on system 10 can allow the purchaser to access to matching algorithm 32 and provide a plurality of exemplary symptoms or disease-states for the particular medical product to the purchaser via the data entry and communication devices 14. In this manner, the purchaser can select one or more symptoms or disease-states from the plurality of exemplary symptoms or disease-states when the one or more symptoms or disease-states match those currently being experienced by the purchaser. Once a symptom or disease-state that the purchaser is experiencing has been selected from the matching algorithm 32, system 10 can operate in the manner discussed herein above. More particularly, system 10 can initiate the use of the selection and/or de-selection algorithms 24, 26, respectively.

Figure 9:
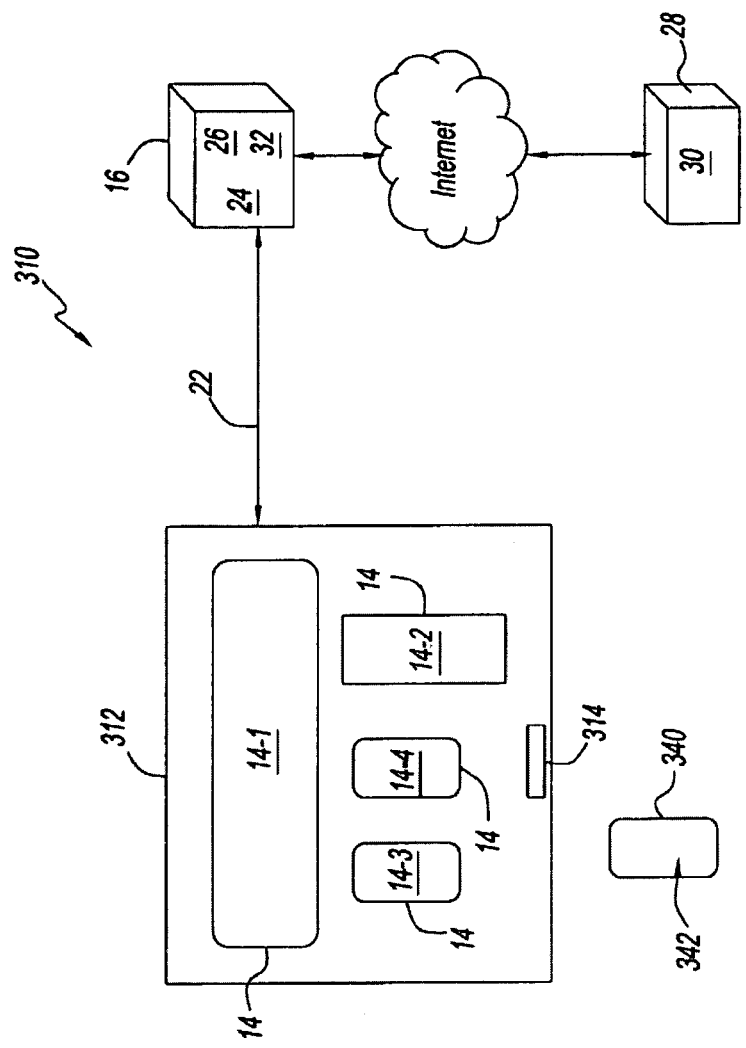
FIGS. 9 through 11 are schematic views illustrating alternate exemplary embodiments of a medical product dispensing system according to the present disclosure.

Referring to the drawings and in particular to FIG. 9, an alternate exemplary embodiment of a medical product dispensing system 310 is shown. For purposes of clarity, a detailed description of component parts in system 310 that perform a similar and/or analogous function as those discussed above with respect to system 10 has been omitted.

Advantageously, system 310 is configured for use in the dispensing of medical products 20b, 20c, and 20d, which have restricted distribution requirements, without the need for interaction between the purchaser and a licensed practitioner. Further, system 310 is configured for use in the dispensing of medical products 20a, which do not have distribution restriction imposed by one or more regulating bodies or authorities, but rather by the retailer and/or product manufacturer. In one embodiment, system 310 provides the purchaser with a printed ticket or transaction record 340, which can be presented to a sales associate, pharmacist or pharmacy personnel located at the point-of-sale. Here, the personnel can retrieve the medical product from a secure location based on the printed ticket or transaction record (hereinafter "record") and complete the transaction. The transaction record 340 can be representative of the medical product or, in some embodiments, can be a proof of purchase of that medical product via system 310. In other embodiments, the transaction record 340 can be the equivalent of a medical questionnaire such as that typically used in the United Kingdom and required by the pharmacist for purchase of behind-the-counter medical products 20c.

Thus, record 340 can be a coupon allowing the holder to purchase the medical product identified on the record. Alternately, system 310 can, upon successful completion of the selection process or de-selection process, require the user to provide electronic payment for the product such that the record 310 is also a receipt for the purchase of the product.

Thus, system 310 provides the purchaser with a printed ticket or transaction record 340, which can be presented to a sales associate, pharmacist or pharmacy personnel located at the point-of-sale along with the medical product itself. Here, the purchaser can retrieve the medical product from a typical store location, present the product and the record to the sales associate at the point-of-sale for completion of the transaction.

In embodiments where record 340 is the coupon allowing the holder to purchase the medical product identified on the record, it is contemplated for the sales associate to be prevented from completing the sales transaction of the medical product without the associated record 340. For example, the associate can be trained to not complete transactions for certain products without the associated record 340. In other examples, the point-of-sale system (not shown) such as the cash register can be configured to prevent transactions for certain products without the associated record 340.

System 310 provides an effective guide to the purchaser through a series of medical history and/or medical product related questions, and also provides product specific information of interest and importance to the information to the purchaser.

Thus, system 310, much like system 10 discussed above, provides an electronic device to significantly reduce the time with or replace a learned intermediary (i.e., licensed practitioner) by capturing the critical elements that a learned intermediary provides, and also provides effective collateral methods for the safe and effective use of a prescription or restricted access medical product in an over the counter environment. Further, system 310 can also be used to help facilitate the purchase of a medical product from a behind-the-counter environment such as that used in the United Kingdom and/or to facilitate the purchase of Schedule 3 and 4 medical products such as those in Australia.

More particularly, system 310 provides an interactive computer having access to one or more of the product specific self-selection algorithm 24, the product specific de-selection algorithm 26, the matching algorithm 32, and any combinations thereof.

However, instead of dispensing the medical products 20a, 20b, 20c, and 20d directly from system 310 as with system 10, system 310 is configured to dispense a record 340 for the medical product selected by a purchaser. Here, system 310 dispenses the record 340 only if the purchaser qualifies for the medical products 20a, 20b, 20c, and 20d as determined by the product specific self-selection algorithm 24, or limited by the label, manufacturer, retailer or other governmental agencies.

Upon subsequent requests for the particular medical product 20a, 20b, 20c, and 20d, the system 310 can dispense a subsequent record 340 for the particular medical product if the purchaser remains qualified for the medical product as determined by the de-selection algorithm 26 in accordance with the prior and new information inputted by the purchaser, or limitations as specified by the label, manufacturer, retailer or other governmental agencies.

Record 340 includes data 342 printed or otherwise recorded thereon. Data 342 can include information such as but not limited to customer identity information, a sales receipt, a product description, a product picture, a purchaser picture, and other data related to the customer, the medical product, or the transaction.

As shown in FIG. 9, system 310 includes a record generating machine 312 having one or more person-machine-interface devices 314. System 310 also includes a controller 16 in communication with record generating machine 312 and one or more interface devices 14-1, 14-2, 14-3, and 14-4.

Record generating machine 312 can also include a printer or encoder 314 and/or can be in electrical communication with the printer or encoder 314 for providing record 340.

In the illustrated embodiment of system 310, controller 16 is shown being remote from record generating machine 312 and communicating with one another via a network 22. However, it is also contemplated by the present disclosure for controller 16 to be resident in record generating machine 312. Moreover, it is contemplated for system 10 to include two controllers, one resident in record generating machine 312 and one remote from the record generating machine 312, where the two controllers communicate over network 22. Network 22 can be any desired communication network such as, but not limited to, a wide-area-network, the Internet, and others.

Figure 10:
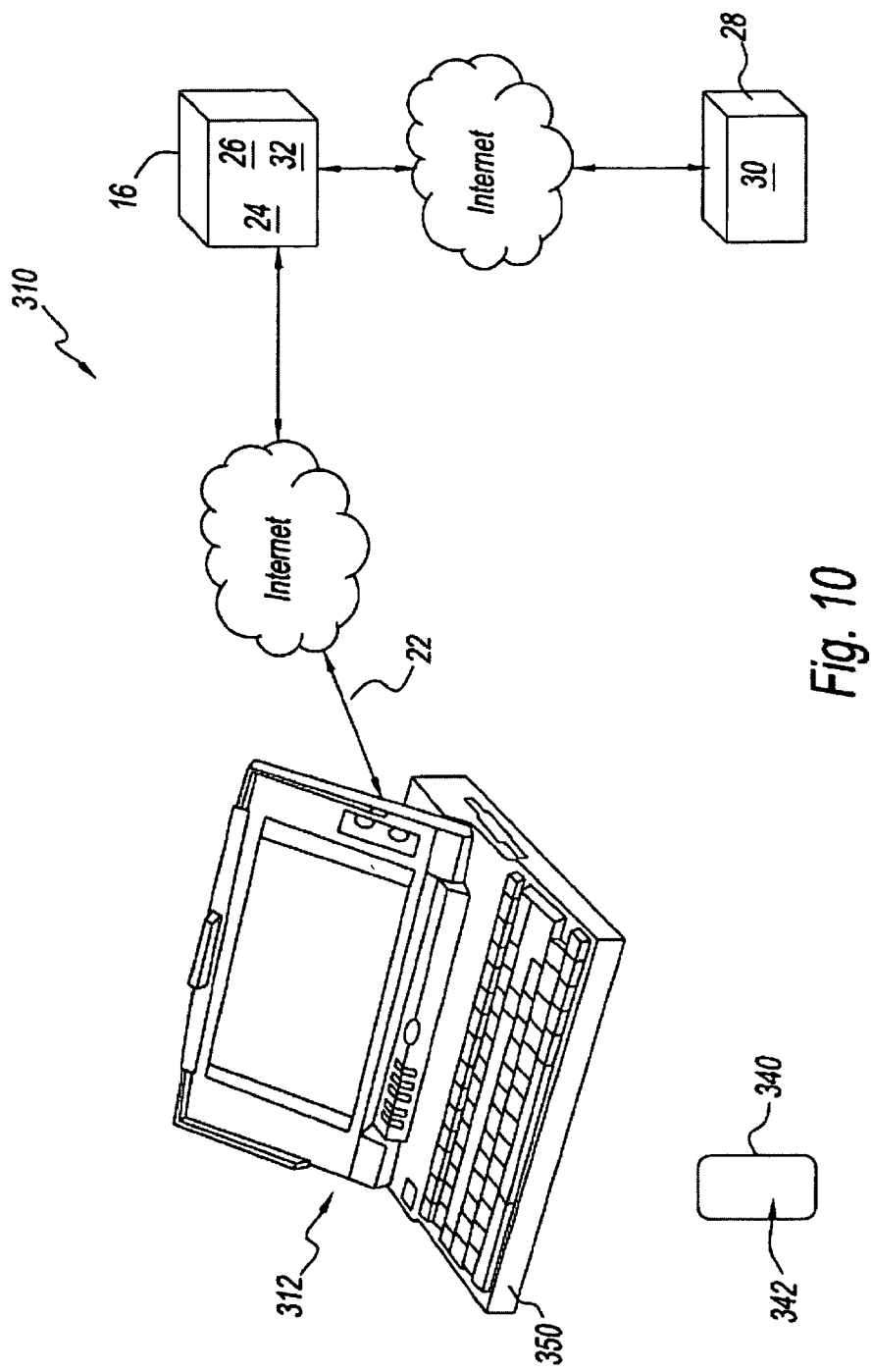

For example, and with reference to FIG. 10, it is contemplated by the present disclosure for record generating machine 312 to be a personal computer 350 communicating with controller 16 over the internet 22. Here, personal computer 350 can be located at the point-of-sale or can be located at the purchasers home, place of business, and the like. Thus, system 310 allows a purchaser to access controller 16 from any desired location via the Internet and after successful interaction with one or more algorithms 24, 26, 32, allows the purchaser to print out the record 340 via a printer (not shown) that reports that the purchaser is eligible and that medical product is acceptable for use. The purchaser then takes the record 340 to a store to purchase the medical product by presenting the record 340 to the store's staff. The presentation of the record 340 to the store's staff can be completed simultaneously to the presentation of the desired product, which the purchaser has retrieved from the store's retail space. Alternately, the record 340 can be presented to the store's staff where upon the staff can retrieve the desired product from a secure location.

System 310 finds use with any of the methods 40, 60, 80, 100, and 150 discussed herein above. However, instead of dispensing the medical product, system 310 generates record 340. Once record 340 has been generated, the purchaser can present the record to a sales associate located at the point-of-sale.

Figure 11:
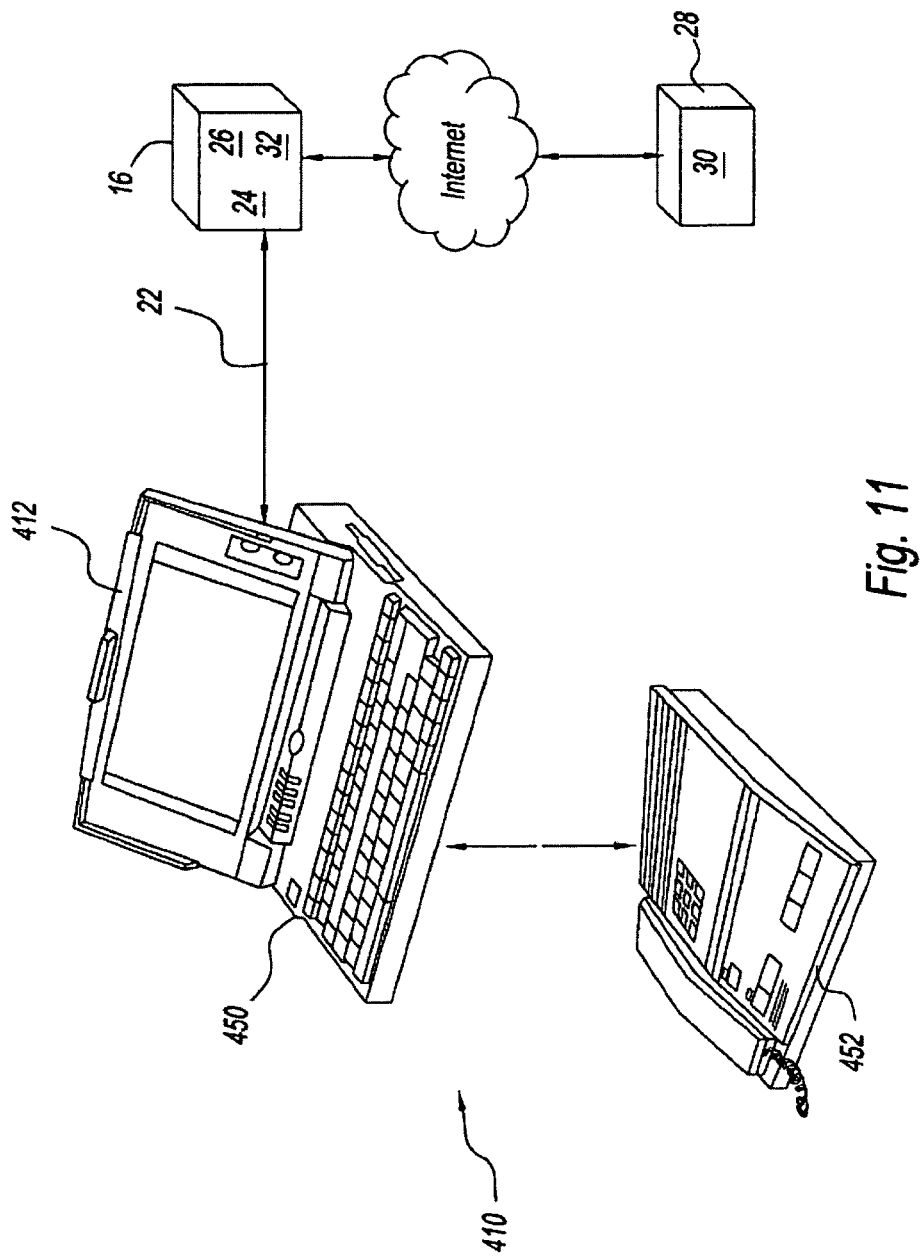

Yet another embodiment of a medical product dispensing system 410 contemplated by the present disclosure is shown in FIG. 11. Here, the consumer "communicates with" or "accesses" controller 16 via a telephone 452. In some embodiments, the consumer communicates with controller 16 directly via an electronic telephone user interface. In other embodiments, the consumer communicates indirectly with controller 16 via a customer service representative, who in-turn communicates with the controller via a computer 450.

Instead of providing a record of the transaction to the purchaser, as described in the embodiments above, the medical product dispensing system 410 mails the purchased product directly to the consumer. Thus, system 410 allows a purchaser to access controller 16 from any desired location and after successful interaction with one or more algorithms 24, 26, 32, allows the purchaser to receive the desired medical product only if that purchaser is eligible and the medical product is acceptable for use.

System 410 finds use with any of the methods 40, 60, 80, 100, and 150 discussed herein above. However, instead of dispensing the medical product, system 410 results in the desired medical product being delivered directly to the purchaser via the mail.

In some embodiments, systems 10, 310, and/or 410 can be configured to ensure compliance with Federal and/or State controlled distribution requirements for medical products 20b such as but not limited to PSE containing products and others. For example, systems 10, 310, and/or 410 can be configured to print and/or report sales transactions to the responsible agency. Systems 10, 310, and/or 410 can be configured to transmit a sales record to another location such as the aforementioned agency that would allow for verification of user and product selected and amount at the point-of-sale. Systems 10, 310, and/or 410 can be configured to collect and report information on particular purchasers' purchasing records for drug products that have potential abuse liabilities. The documentation may include quantities of product sold, date sold and total number of products sold.

Accordingly, one embodiment of the present disclosure is directed to a method for dispensing medical products, includes: identifying a particular medical product having a distribution restricted status; placing a vending machine in a general sales location, the vending machine having a person-machine-interface device in communication with a controller; storing a supply of the particular medical product in the vending machine; storing an electronic self-selection process on the controller; and controlling the vending machine, via the controller, to dispense a first sales unit of the particular medical product only if a purchaser successfully completes the self-selection process for an initial purchase request for the particular medical product via the interface device.

In one embodiment of the above noted method, the particular medical product includes a non-prescription, behind-the-counter medical product or an over-the-counter, non-prescription medical product. In some embodiments, the method can further include storing an electronic de-selection process on the controller and, if desired, can include controlling the vending machine, via the controller, to dispense a second or subsequent sales unit of the particular medical product only if the purchaser successfully completes the de-selection process for a second or subsequent purchase request for the particular medical product via the purchaser interface. In other embodiments, the method further includes collecting biometric data from the purchaser as part of the de-selection process and, if desired, can include analyzing the biometric data from the purchaser as part of the de-selection process. In still further embodiments, the method further includes providing information to the purchaser and, if desired, can includes customizing the information based on the self-selection process, the de-selection process, and any combinations thereof and/or including customizing the information based on biometric data. In yet another embodiment, the method further includes controlling the vending machine, via the controller, to provide instructions to the purchaser in the event that the controller determines that the purchaser did not successfully complete the de-selection process, the instructions including steps needed to successfully complete the de-selection process. In still another further embodiment, the de-selection process can include automatically limiting a length of therapy of the particular medical product to a predetermined length.

In another embodiment of the above noted method, the method further includes collecting information from the purchaser as part of the self-selection process. The method can further include collecting purchaser specific biometric data from the purchaser as part of the self-selection process. In some embodiments, collecting the biometric data includes measuring the biometric data at the vending machine. In other embodiments, the method can further include analyzing the biometric data from the purchaser as part of the self-selection process. In other embodiments, collecting the biometric data includes requesting the purchaser to manually enter the biometric data into the vending machine or scanning the biometric data into the vending machine from a user provided medium. In still further embodiments, collecting the biometric data can include: requesting the purchaser to place a purchaser supplied biometric measurement device in electrical communication with the vending machine; and controlling the vending machine to retrieve the biometric data from the purchaser supplied biometric measurement. In yet another embodiment, collecting the biometric data can include: storing the biometric data on a database associated with an external test or laboratory site; and authorizing, during the self-selection process, the vending machine to access the biometric data on the database via a network connection.

In a further embodiment of the above noted method, the method can further include providing warning and caution data to the purchaser during the self-selection process.

In an alternate embodiment of the above noted method, the method can further include controlling the vending machine, via the controller, to provide instructions to the purchaser in the event that the controller determines that the purchaser did not successfully complete the self-selection process, the instructions including steps needed to successfully complete the self-selection process. In some embodiments, the instructions can include instructions to seek medical advice.

In another alternate embodiment of the above noted method, the particular medical product includes a prescription product.

Accordingly, a second embodiment is directed to a method of dispensing a medical product from a vending machine in a general sales location, including: accepting a purchase request at the vending machine from a purchaser for a particular restricted distribution medical product; determining if the purchase request is an initial purchase request or a subsequent purchase request by the purchaser for the particular medical product; accessing a self-selection algorithm for the particular medical product if the purchase request is the initial purchase request; accessing a de-selection algorithm for the particular medical product if the purchase request is the subsequent purchase request; requiring the purchaser to input an answer to each of a plurality of questions generated by the self-selection algorithm or the de-selection algorithm; and controlling the vending machine, via the self-selection algorithm or the de-selection algorithm, to dispense or not dispense the particular medical product based the answers.

In one embodiment of the above noted method, the method further includes retrieving stored data from the answers of the purchaser if the purchase request is the subsequent purchase request.

In a different embodiment of the above noted method, the method further includes contacting the purchaser, based on information for the purchaser, after the self-selection algorithm or the de-selection algorithm dispenses the particular medical product.

In another embodiment of the above noted method, the step of requiring the purchaser to input the answers further includes collecting biometric data from the purchaser. The step of collecting the biometric data can include measuring the biometric data at the vending machine, requesting the purchaser to manually enter the biometric data into the vending machine, or requesting the purchaser to scan or read the biometric data into the vending machine. In other embodiments, the step of collecting the biometric data can include: requesting the purchaser to place a purchaser supplied biometric measurement device in electrical communication with the vending machine; and controlling the vending machine to retrieve the biometric data from the purchaser supplied biometric measurement. Also, the step of collecting the biometric data can include: storing the biometric data on a database associated with an external test or laboratory site; and requiring the purchaser to authorize, as part of the answers, the vending machine to access the biometric data on the database via a network connection.

Accordingly, another embodiment of the present disclosure is directed to a method of dispensing a medical product from a vending machine in a general sales location, including: accepting a purchase request at a vending machine from a purchaser for a particular medical product; accessing a dispensing algorithm for the particular medical product; requiring the purchaser to input an answer to each of a plurality of questions generated by the dispensing algorithm; collecting biometric data from the purchaser; and determining whether or not to dispense the particular medical product based on the answers and based, at least in part, on the biometric data.

In one embodiment of the above noted method, the particular medical product can be a restricted sales medical product or a non-prescription medical product.

In another embodiment of the above noted method, the step of collecting the biometric data includes measuring the biometric data at the vending machine or requesting the purchaser to manually enter the biometric data into the vending machine or requesting the purchaser to scan or read the biometric data into the vending machine.

In yet another embodiment of the above noted method, the step of collecting the biometric data includes requesting the purchaser to place a purchaser supplied biometric measurement device in electrical communication with the vending machine; and controlling the vending machine to retrieve the biometric data from the purchaser supplied biometric measurement.

In still another embodiment of the above noted method, the step of collecting the biometric data includes storing the biometric data on a database associated with an external test or laboratory site; and authorizing, during the self-selection process, the vending machine to access the biometric data on the database via a network connection.

In still a further embodiment of the above noted method, the method includes customizing one or more attributes of the purchase request based, at least in part, on the biometric data. Here, the one or more attributes can include a dosage of the medical product, a use instruction, a warning, and any combinations thereof.

Accordingly, yet another embodiment of the present disclosure is directed to a method of switching a prescription medical product to a non-prescription, over-the-counter medical product, including: selecting a particular medical product having a prescription status; developing a set of initial dispensing criteria for the particular medical product, the set of initial dispensing criteria that is sufficient so that a responsible regulatory agency approves a change in status of the particular medical product to a non-prescription status; developing a set of product specific and purchaser specific self-selection questions based on the set of initial dispensing criteria; arranging the set of self-selection questions into a self-selection algorithm; placing the particular medical product in a vending machine having a person-machine-interface device in electrical communication with a controller; placing the vending machine in a general sales location; storing the self-selection algorithm on the controller; and controlling the vending machine, via the controller, to dispense a first sales unit of the particular medical product only if a purchaser successfully completes the self-selection algorithm via the interface device.

In one embodiment of the above noted method, the method further includes restricting a number of units of sales to the purchaser.

In another embodiment of the above noted method, the method further includes: developing a set of subsequent dispensing criteria for the particular medical product, the set of subsequent dispensing criteria being sufficient to the responsible regulatory agency to allow or maintain the non-prescription status; developing a set of product specific and purchaser specific de-selection questions based on the set of subsequent dispensing criteria; arranging the set of de-selection questions into a de-selection algorithm; storing the de-selection algorithm on the controller; and controlling the vending machine, via the controller, to dispense a subsequent sales unit of the particular medical product only if the purchaser successfully completes the de-selection algorithm via the interface device.

Accordingly, a further embodiment of the present disclosure is directed to a medical product dispensing system, including: a vending machine defining a storage space, the storage space being configured to receive one or more restricted distribution medical products and one or more unrestricted distribution medical products therein; one or more person-machine-interface devices; a controller in communication with the vending machine and the one or more interface devices; and a self-selection algorithm resident on the controller for each of the restricted distribution medical products in the storage space, wherein the controller is configured, upon selection of a particular restricted distribution medical product by a purchaser via the one or more interface devices, to determine whether the selection of the particular restricted distribution medical product is a first request or a second request for the particular restricted distribution medical product, wherein the controller is configured to require the purchaser to complete the self-selection algorithm if the request is the first request, and wherein the controller is configured to dispense the particular restricted distribution medical product only if the purchaser successfully completes the self-selection algorithm.

In one embodiment of the above noted system, the controller is configured to require the purchaser to enter information personal to the purchaser via the one or more interface devices and wherein the controller is configured to determine, based on the selection of the restricted distribution medical product and the information personal to the purchaser, whether the selection of the particular restricted distribution medical product is the first request or the second request.

In another embodiment of the above noted system, the system further includes a de-selection algorithm resident on the controller for each restricted distribution medical product in the storage space, wherein the controller is configured to require the purchaser to complete the de-selection algorithm if the request is the second request and wherein the controller is configured to dispense the particular restricted distribution medical product only if the purchaser successfully completes the de-selection algorithm.

In a further embodiment of the above noted system, the controller is configured, upon selection of a particular unrestricted distribution medical product by the purchaser via the one or more interface devices, to distribute the particular unrestricted distribution medical product without requiring entry of additional purchaser information.

In still a further embodiment of the above noted system, the self-selection algorithm is dependent only on an age of the purchaser or is dependent only on an identity of the purchaser, an age of the purchaser, and a number of purchases of the particular restricted distribution medical product medical product by the purchaser within a predetermined period of time when the particular restricted distribution medical product includes pseudoephedrine or any age restricted medical product. In some embodiments, the controller can be in electrical communication with a plurality of vending machines, the controller storing information regarding each purchaser at the plurality of vending machines so that the number of purchases of the particular restricted distribution medical product is based on purchases by the purchaser at the plurality of vending machines.

In yet another embodiment of the above noted system, the one or more interface devices include one or more data entry and communication devices. In some embodiments, the data entry and communication devices can include a device selected from the group consisting of a visual display screen, a standard alphanumeric key board, a mouse or pointing device, a touch screen, a credit card reader, a bar code reader, a speaker, a microphone, a voice recognition device, a printer, a wired communication port, a wireless communication port, and any combinations thereof. In other embodiments, the controller is configured to control the one or more data entry and communication devices, when the vending machine is not in use, to provide advertising, drug promotion, and/or drug information to people in the vicinity of the vending machine.

In another embodiment of the above noted system, the interface devices include one or more identification devices and, in some embodiments, the identification devices is selected from the group consisting of a magnetic stripe reader, a bar code reader, a finger print scanner, a retinal scanners, a facial recognition device, a DNA scanner, and any combinations thereof. In this embodiment, it is contemplated for the self-selection algorithm to require biometric data and for the controller to be configured to dispense the particular restricted distribution medical product only if the biometric data meets to biometric data parameters in the self-selection algorithm. In some embodiments, the biometric data is read from a user supplied medical history card or medical diagnosis card by said device.

In still another embodiment of the above noted system, the one or more interface devices include one or more biometric data devices. In some embodiments, the self-selection algorithm requires biometric data and wherein the controller is configured to dispense the particular restricted distribution medical product only if the biometric data meets to biometric data parameters in the self-selection algorithm. In other embodiments, the one or more biometric data devices include a device selected from the group consisting of a blood pressure monitor, a blood glucose monitor, a thermometer, an infrared blood gas analyzer, and any combinations thereof.

In yet another embodiment of the above noted system, the one or more interface devices include one or more payment devices. In some embodiments, the one or more payment devices include a device selected from the group consisting of a credit reader, a debit card reader, a cash accepting device, a coin accepting device, and any combinations thereof. In other embodiments, the controller is configured to determine a cost for the medical product based on insurance provider information entered by the purchaser.

In further embodiments of the above noted system, the controller can be configured to communicate with a database at an external test or laboratory site to obtain biometric data of the purchaser upon authorization by the purchaser via the one or more interface devices or can be configured to control the storage space to store the one or more medical products at an ambient storage condition, a conditioned storage condition, or any combinations thereof.

In still further embodiments of the above noted system, the storage space includes a plurality of storage spaces and the vending machine and/or the controller can be configured to control the plurality of storage spaces to store the one or more medical products at conditions appropriate for each medical product, while in some embodiments, the plurality of storage spaces include an auxiliary device attached to the dispensing unit.

In yet a further embodiment of the above noted system, the vending machine includes one or more sensors in communication with the controller, the controller being configured to monitor an internal inventory of medical products within the storage space via the one or more sensors.

Accordingly, a further embodiment of the present disclosure is directed to a method for distributing a medical product, including: providing a controller having a matching algorithm resident thereon; allowing a purchaser to access to the matching algorithm; controlling the matching algorithm to provide a plurality of exemplary symptoms or disease-states to the purchaser via at least one data entry and communication device in visual or auditory form; allowing the purchaser to select one or more symptoms or disease-states from the plurality of exemplary symptoms or disease-states when the one or more symptoms or disease-states match those currently being experienced by the purchaser; and controlling the matching algorithm to provide a list of one or more appropriate medical products for the one or more symptoms or disease-states selected.

In one embodiment of the above noted method, the method further includes: allowing the purchaser to select a particular medical product from the list; and controlling a vending machine to dispense the particular medical product. In some embodiments, the step of controlling the vending machine to dispense the particular medical product includes: accessing a self-selection algorithm for the particular medical product if the purchase request is the initial purchase request; and controlling the vending machine, via the controller, to dispense a first sales unit of the particular medical product only if purchaser successfully completes the self-selection algorithm via the at least one data entry and communication device. In other embodiments, the step of controlling the vending machine to dispense the particular medical product includes: accessing a de-selection algorithm for the particular medical product if the purchase request is the second purchase request; and controlling the vending machine, via the controller, to provide the particular medical product only if the purchaser successfully completes the de-selection process via the at least one data entry and communication device. In this embodiment, the step of controlling the vending machine to dispense the particular medical product can further include: collecting biometric data from the purchaser; and determining whether or not to dispense the particular medical product based on the answers and based, at least in part, on the biometric data.

In another embodiment of the above noted method, the method further includes: allowing the purchaser to select a particular medical product from the list; and controlling the controller to provide a transaction record of the particular medical product. Here, the step of controlling the vending machine to dispense the particular medical product can include: accessing a self-selection algorithm for the particular medical product if the purchase request is the initial purchase request; and controlling the vending machine, via the controller, to dispense a first sales unit of the particular medical product only if the purchaser successfully completes the self-selection algorithm via the at least one data entry and communication device. Further, the step of controlling the vending machine to dispense the particular medical product can include: accessing a de-selection algorithm for the particular medical product if the purchase request is the second purchase request; and controlling the vending machine, via the controller, to provide the particular medical product only if the purchaser successfully completes the de-selection process via the at least one data entry and communication device. Also, the step of controlling the vending machine to dispense the particular medical product can further include: collecting biometric data from the purchaser; and determining whether or not to dispense the particular medical product based on the answers and based, at least in part, on the biometric data. In other embodiments, the method can further include requiring the purchaser to take the transaction record to a sales associate, the sales associate providing the purchaser with the particular product only upon receipt of the transaction record and/or requiring the purchaser to retrieve the particular product from a retail shelf; and requiring the purchaser to take the transaction record and the particular product to a sales associate.

In still another embodiment of the above noted method, the step of controlling the symptom matching algorithm to provide the plurality of exemplary symptoms includes: controlling the at least one data entry and communication device to play a sample sound for the purchaser and, in some embodiments, the sample sound includes sound selected from the group consisting of a loose cough, a dry cough, and any combinations thereof.

In still further embodiments of the above noted method, the step of controlling the symptom matching algorithm to provide the list of one or more appropriate medical products for the one or more symptoms selected includes: presenting only those medical products that do not have adverse interactions with medical products currently being used by the purchaser or medical conditions experienced by the purchaser. Alternately, the step of controlling the symptom matching algorithm to provide the list of one or more appropriate medical products for the one or more symptoms selected can include: presenting only those medical products that do not have adverse interactions with medical conditions experienced by the purchaser.

Accordingly, still a further embodiment of the present disclosure is directed to a method for distributing a particular medical product, including: providing a controller having a matching algorithm resident thereon for the particular medical product; allowing a purchaser to access to the matching algorithm; controlling the matching algorithm to provide a plurality of exemplary symptoms or disease-states for the particular medical product to the purchaser via at least one data entry and communication device; allowing the purchaser to select one or more symptoms or disease-states from the plurality of exemplary symptoms or disease-states when the one or more symptoms or disease-states match those currently being experienced by the purchaser; and determining if the purchase request is an initial purchase request or a subsequent purchase request by the purchaser for the particular medical product; accessing a self-selection algorithm for the particular medical product if the purchase request is the initial purchase request; accessing a de-selection algorithm for the particular medical product if the purchase request is the subsequent purchase request; requiring the purchaser to input an answer to each of a plurality of questions generated by the self-selection algorithm or the de-selection algorithm; and allowing, via the self-selection algorithm or the de-selection algorithm, the purchaser to purchase the particular medical product based the answers.

In one embodiment of the above noted method, the step of allowing the purchaser to purchase the particular medical product includes controlling the vending machine, via the self-selection algorithm or the de-selection algorithm, to dispense or not dispense the particular medical product based the answers.

In another embodiment of the above noted method, the step of allowing the purchaser to purchase the particular medical product includes controlling the vending machine, via the self-selection algorithm or the de-selection algorithm, to dispense or not dispense a transaction record representative of the particular medical product based the answers.

It is of course contemplated by the present disclosure that all of these embodiments may be used in combination with each other in any desired manner.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. A method for distributing a restricted distribution medical product, comprising:

storing an electronic self-selection algorithm related to the restricted distribution medical product on a controller connected to an interactive computer controlled device, wherein the electronic self-selection algorithm evaluates (1) information identified by a governmental agency and included on the label of the restricted distribution medical product and (2) information provided by a potential purchaser relating to the potential purchaser's medical condition including areas of critical interest related to the potential purchaser's medical history and signs and symptoms of the condition to be treated and, based on the evaluation, determines whether there is a benefit of starting treatment with the restricted distribution medical product and whether the benefit outweighs the risks associated with not starting treatment;

completing by the potential purchaser through the device, an electronic self-selection process according to the electronic self-selection algorithm, for a first purchase of the restricted distribution medical product;

generating, by the controller, based on the completed electronic self-selection process, a transaction record for the restricted distribution medical product, without interaction between the potential purchaser and a licensed practitioner, for the first purchase request for the restricted distribution medical product;

storing an electronic de-selection algorithm related to the restricted distribution medical product, wherein the electronic de-selection algorithm evaluates (1) updated information provided by the potential purchaser relating to the potential purchaser's medical condition updated to the present including different areas of critical interest from that of the electronic self-selection algorithm and (2) past use of the restricted distribution medical product and, based on the evaluation, determines whether there is a benefit to continue treatment with the restricted distribution medical product and whether the benefit outweighs the risks associated with not continuing treatment;

unsuccessfully performing by the potential purchaser through the device, an electronic de-selection process according to the electronic de-selection algorithm, for a second or subsequent purchase request of the restricted distribution medical product; and denying by the controller based on the unsuccessfully performed electronic de-selection process, the second or subsequent purchase request of the restricted distribution medical product, without interaction between the potential purchaser and a licensed practitioner, when the potential purchaser failed to successfully complete the electronic de-selection process.

2. The method of claim 1, further comprising collecting information from the potential purchaser as part of the electronic self-selection process.

3. The method of claim 2, further comprising customizing the information based on the electronic self-selection process, the electronic de-selection process, and any combinations thereof.

4. The method of claim 2, further comprising customizing the information based on purchaser specific biometric data.

5. The method of claim 1, further comprising:

allowing the purchaser to purchase the restricted distribution medical product if the potential purchaser successfully completes the electronic self-selection process or the electronic de-selection process.

6. The method of claim 5, wherein the transaction record includes proof of purchase of the restricted distribution medical product.

7. The method of claim 6, further comprising:
requiring the potential purchaser to present the transaction record at a point-of-sale.

8. The method of claim 1, further comprising collecting purchaser specific biometric data from the potential purchaser as part of the electronic self-selection process, wherein the biometric data is representative of one or more physiological conditions of the potential purchaser.

9. The method of claim 8, wherein collecting the biometric data comprises controlling the controller to measure the biometric data of the potential purchaser.

10. The method of claim 8, further comprising analyzing the purchaser specific biometric data as part of the electronic self-selection process.

11. The method of claim 8, wherein collecting the purchaser specific biometric data comprises requesting the potential purchaser to manually enter the biometric data into the controller.

12. The method of claim 8, wherein collecting the purchaser specific biometric data comprises allowing the potential purchaser to scan or read the biometric data into the controller from a user provided medium.

13. The method of claim 8, wherein collecting the purchaser specific biometric data comprises:
requesting the potential purchaser to place a purchaser supplied biometric measurement device in electrical communication with the controller; and
controlling the controller to retrieve the purchaser specific biometric data from the potential purchaser supplied biometric measurement device.

14. The method of claim 8, wherein collecting the purchaser specific biometric data comprises:
storing the purchaser specific biometric data on a database associated with an external test or laboratory site; and
authorizing, by the electronic self-selection process, the controller to access the purchaser specific biometric data on the database via a network connection.

15. The method of claim 1, wherein the restricted distribution medical product comprises a non-prescription, behind-the-counter medical product.

16. The method of claim 1, further comprising controlling the controller to provide instructions to the potential purchaser in the event that the controller determines that the potential purchaser did not successfully complete the electronic self-selection process, the instructions including steps needed to successfully complete the electronic self-selection process.

17. The method of claim 1, further comprising controlling the controller to provide instructions to the potential purchaser in the event that the controller determines that the potential purchaser did not successfully complete the electronic de-selection process, the instructions including steps needed to successfully complete the electronic de-selection process.

18. The method of claim 1, wherein the electronic de-selection process comprises automatically limiting a length of therapy of the restricted distribution medical product to a predetermined length.

19. The method of claim 1, further comprising providing warning and caution data to the potential purchaser as part of the electronic self-selection process and/or the electronic de-selection process.

20. The method of claim 1, wherein allowing the potential purchaser of the restricted distribution medical product to access the electronic self-selection and electronic de-selection processes comprises:
allowing the potential purchaser of the restricted distribution medical product to access the electronic self-selection and electronic de-selection processes via the Internet.

21. The method of claim 1, further comprising:
requiring the potential purchaser to retrieve the restricted distribution medical product from a retail shelf in a retail location; and
requiring the potential purchaser to take the transaction record and the restricted distribution medical product to a sales associate at the retail location.

22. A method for distributing a restricted distribution medical product, comprising:
storing an electronic self-selection algorithm related to the restricted distribution medical product on a controller of an interactive device, wherein the electronic self-selection algorithm evaluates (1) information identified by a governmental agency and included on the label of the restricted distribution medical product and (2) information provided by a purchaser relating to the purchaser's medical condition including areas of critical interest related to the purchaser's medical history and signs and symptoms of the condition to be treated and, based on the evaluation, determines whether there is a benefit of starting, that outweighs the risk of not starting, treatment with the restricted distribution medical product;
completing by a purchaser of the restricted distribution medical product to access and complete, via a telephone operatively connected to the interactive device, the electronic self-selection algorithm for a first purchase request of the restricted distribution medical product;
generating, by the controller, based on the completed electronic self-selection process, a transaction record for the restricted distribution medical product without interaction between the purchaser and a licensed practitioner, for the first purchase request for the restricted distribution medical product;
storing an electronic de-selection algorithm related to the restricted distribution medical product on the controller, wherein the electronic de-selection algorithm evaluates (1) updated information provided by the purchaser relating to the purchaser's medical condition updated to the present including different areas of critical interest from that of the electronic self-selection algorithm and (2) past use of the restricted distribution medical product and, based on the evaluation, determines whether there is a benefit, that outweighs the risk, to continue treatment with the restricted distribution medical product;
unsuccessfully performing by the purchaser through the device, an electronic de-selection process according to the electronic de-selection algorithm, for a second or subsequent purchase request for the restricted distribution medical product; and
denying by the controller based on the unsuccessfully performed electronic de-selection process, the second or subsequent purchase request of the restricted distribution medical product, without intervention between purchaser and a licensed practitioner, when the purchaser fails to successfully complete the electronic de-selection process.

23. The method of claim 22, further comprising collecting purchaser specific biometric data from the potential purchaser as part of completing the electronic self-selection process.

24. The method of claim 23, further comprising analyzing the purchaser specific biometric data as part of the electronic self-selection process.

25. The method of claim 23, wherein collecting the purchaser specific biometric data comprises requesting the purchaser to manually enter the biometric data into the controller.

26. The method of claim 22, wherein the restricted distribution medical product comprises a non-prescription, behind-the-counter medical product.

27. The method of claim 22, further comprising collecting information from the purchaser as part of completing the electronic self-selection process.

28. A method for dispensing a restricted distribution medical product, comprising:
   identifying a restricted distribution medical product having a restricted distribution status;
   placing a vending machine in a general sales location, the vending machine having a person-machine-interface device in communication with a controller;
   storing a supply of the restricted distribution medical product in the vending machine;
   storing an electronic self-selection process related to the restricted distribution medical product on the controller, wherein the electronic self-selection includes an algorithm evaluates (1) information identified by a governmental agency and included on the label of the restricted distribution medical product and (2) information provided by a purchaser relating to the purchaser's medical condition including areas of critical interest related to the purchaser's medical history and signs and symptoms of the condition to be treated and, based on the evaluation, determines whether there is a benefit of starting, that outweighs the risks associated with not starting, treatment with the restricted distribution medical product;
   controlling the vending machine, via the controller, to dispense a first sales unit of the restricted distribution medical product, without interaction between the purchaser and a licensed practitioner when the purchaser successfully completes the electronic self-selection process for an initial purchase request for the restricted distribution medical product;
   controlling the vending machine, via the controller, not to dispense the first sales unit of the restricted distribution medical product when the purchaser does not successfully completes the electronic self-selection process;
   storing an electronic de-selection process including an algorithm related to the restricted distribution medical product on the controller, wherein the electronic de-selection algorithm evaluates (1) updated information provided by the purchaser relating to the purchaser's medical condition updated to the present including different areas of critical interest from that of the electronic self-selection algorithm and (2) past use of the restricted distribution medical product and, based on the evaluation, determines whether there is a benefit to continue, that outweighs the risks associated with not continuing, treatment with the restricted distribution medical product;
   unsuccessfully performing by the purchaser through the vending machine, an electronic de-selection process according to the electronic de-selection algorithm, for a second or subsequent purchase request for the restricted distribution medical product; and
   denying by the controller based on the unsuccessfully performed electronic de-selection process, the second or subsequent purchase request of the restricted distribution medical product, without intervention between the purchaser and a licensed practitioner, when the purchaser failed to successfully complete the electronic de-selection process.

29. A method of dispensing a restricted distribution medical product from a vending machine in a general sales location, comprising:
   accepting a purchase request at the vending machine from a purchaser for a restricted distribution medical product;
   accessing a dispensing process of the vending machine for the restricted distribution medical product, wherein the dispensing process stores an electronic self-selection algorithm related to the restricted distribution medical product, and requires the purchaser to input an answer to each of a plurality of questions, wherein the electronic self-selection algorithm evaluates (1) information identified by a governmental agency and included on the label of the restricted distribution medical product and (2) information provided by the purchaser relating to the purchaser's medical condition including areas of critical interest related to the purchaser's medical history and signs and symptoms of the condition to be treated and biometric data being representative of one or more physiological conditions of the purchaser, and, based on the evaluation, determines whether there is a benefit of starting, that outweighs the risks associated with not starting, treatment with the restricted distribution medical product;
   dispensing the restricted distribution medical product, without interaction between the purchaser and a licensed practitioner based, at least in part, on the biometric data and answers input by the purchaser;
   accessing a second or subsequent dispensing process of the vending machine for the restricted distribution medical product, wherein the dispensing process stores an electronic de-selection algorithm related to the restricted distribution medical product on the controller, wherein the electronic de-selection algorithm evaluates (1) updated information provided by the purchaser relating to the purchaser's medical condition updated to the present including different areas of critical interest from that of the electronic self-selection algorithm and (2) past use of the restricted distribution medical product and, based on the evaluation, determines whether there is a benefit to continue, that outweighs the risks associated with not continuing, treatment with the restricted distribution medical product;
   unsuccessfully performing through the vending machine, an electronic de-selection process according to the electronic de-selection algorithm, for a second or subsequent purchase request for the restricted distribution medical product; and
   denying by the vending machine based on the unsuccessfully performed electronic de-selection process, the second or subsequent purchase request of the restricted distribution medical product, without intervention between the purchaser and a licensed practitioner, when the purchaser failed to successfully complete the electronic de-selection process.

30. A method of switching a prescription medical product to a non-prescription, restricted distribution medical product and dispensing same, comprising:

selecting a medical product having a prescription status;
developing a set of initial dispensing criteria for the medical product, the set of initial dispensing criteria being sufficient so that a responsible regulatory agency approves a change in status of the medical product to a non-prescription status for restricted distribution;
developing a set of product specific and purchaser specific self-selection questions based on the set of initial dispensing criteria;
arranging the set of self-selection questions into an electronic self-selection process having an electronic self-selection algorithm related to the restricted distribution medical product on a controller of a vending machine, wherein the electronic self-selection algorithm evaluates (1) information identified by a governmental agency and included on the label of the medical product and (2) information provided by a purchaser relating to the purchaser's medical condition including areas of critical interest related to the purchaser's medical history and signs and symptoms of the condition to be treated and, based on the evaluation, determines whether there is a benefit of starting, that outweighs the risks associated with not starting, treatment with the medical product;
controlling the vending machine, via the controller, to dispense a first sales unit of the restricted distribution medical product, without interaction between the purchaser and a licensed practitioner, when a purchaser successfully completes the electronic self-selection process and not to dispense the first sales unit of the restricted distribution medical product when the purchaser does not successfully completes the electronic self-selection process;
arranging the set of de-selection questions into an electronic de-selection process having a de-selection algorithm related to the restricted distribution medical product on the controller, wherein the electronic de-selection algorithm evaluates (1) updated information provided by the purchaser relating to the purchaser's medical condition updated to the present including different areas of critical interest from that of the electronic self-selection algorithm and (2) past use of the restricted distribution medical product and, based on the evaluation, determines whether there is a benefit to continue, that outweighs the risks associated with not continuing, treatment with the restricted distribution medical product;
unsuccessfully performing through the vending machine, an electronic de-selection process according to the electronic de-selection algorithm, for a second or subsequent purchase request for the restricted distribution medical product; and
denying by the vending machine based on the unsuccessfully performed electronic de-selection process, the second or subsequent purchase request of the restricted distribution medical product, without intervention between the purchaser and a licensed practitioner, when the purchaser failed to successfully complete the electronic de-selection process.

31. A restricted distribution medical product dispensing system, comprising:
a vending machine defining a storage space, the storage space being configured to receive one or more restricted distribution medical products and one or more unrestricted distribution medical products therein;
one or more person-machine-interface devices;
a controller in communication with the vending machine and the one or more interface devices;
the controller configured to store an electronic self-selection process for each of the restricted distribution medical products in the storage space, wherein the electronic self-selection algorithm evaluates (1) information identified by a governmental agency and included on the label of the medical product and (2) information provided by a potential purchaser relating to the potential purchaser's medical condition including areas of critical interest related to the potential purchaser's medical history and signs and symptoms of the condition to be treated and, based on the evaluation, determines whether there is a benefit of starting treatment with the restricted distribution medical product and whether the benefit outweighs the risks associated with not starting treatment,
wherein the controller is configured, upon selection of the restricted distribution medical product by the potential purchaser via the one or more interface devices, to determine whether the selection of the particular restricted distribution medical product is a first request or a second or subsequent request for the restricted distribution medical product,
wherein the controller is configured to require the potential purchaser to complete the electronic self-selection process for the first request,
wherein the controller is configured to dispense the restricted distribution medical product without interaction between the potential purchaser and a licensed practitioner, when the potential purchaser successfully completes the electronic self-selection process, and
wherein the controller is configured not to dispense the restricted distribution medical product should the potential purchaser not successfully complete the electronic self-selection process;
the controller configured to store an electronic de-selection algorithm for each of the restricted distribution medical products in the storage space, wherein the electronic de-selection algorithm evaluates (1) updated information provided by the potential purchaser relating to the potential purchaser's medical condition updated to the present including different areas of critical interest from that of the electronic self-selection algorithm and (2) past use of the restricted distribution medical product and, based on the evaluation, determines whether there is a benefit to continue treatment with the restricted distribution medical product and whether the benefit outweighs the risks associated with not continuing treatment;
the controller configured to receive input of an unsuccessfully performed electronic de-selection process according to the electronic de-selection algorithm, for a second or subsequent purchase request for the restricted distribution medical product; and
the controller, based on the unsuccessfully performed electronic de-selection process, configured to deny the second or subsequent purchase request of the restricted distribution medical product, without intervention between the potential purchaser and a licensed practitioner, when the potential purchaser failed to successfully complete the electronic de-selection process.

32. A method of switching a behind-the-counter medical product to non-prescription, restricted distribution medical product and the dispensing of same, comprising:
selecting a medical product having a behind-the-counter status;
developing a set of initial dispensing criteria for the medical product, the set of initial dispensing criteria being sufficient so that a responsible regulatory agency approves a change in status of the medical product to nonprescription status for restricted distribution;

developing a set of self-selection questions based on the set of initial dispensing criteria;

arranging the set of self-selection questions into an electronic self-selection algorithm on a controller connected to a machine interface device of a vending machine, wherein the electronic self-selection algorithm evaluates (1) information identified by a governmental agency and included on the label of the restricted distribution medical product and (2) information provided by a purchaser relating to the purchaser's medical condition including areas of critical interest related to the purchaser's medical history and signs and symptoms of the condition to be treated and, based on the evaluation, determines whether there is a benefit of starting treatment with the restricted distribution medical product and whether the benefit outweighs the risks associated with not starting treatment;

controlling the vending machine, via the controller, to dispense a first sales unit of the restricted distribution medical product, without interaction between the purchaser and a licensed practitioner, when a purchaser successfully completes the electronic self-selection process;

controlling the vending machine, via the controller, not to dispense the first sales unit of the restricted distribution medical product should the purchaser not successfully complete the electronic self-selection process;

storing an electronic de-selection algorithm on the controller for the restricted distribution medical product, wherein the electronic de-selection algorithm evaluates (1) updated information provided by the purchaser relating to the purchaser's medical condition updated to the present including different areas of critical interest from that of the electronic self-selection algorithm and (2) past use of the medical product and, based on the evaluation, determines whether there is a benefit to continue treatment with the restricted distribution medical product and whether the benefit outweighs the risks associated with not continuing treatment;

unsuccessfully performing through the controller, the electronic de-selection algorithm, for a second or subsequent purchase request for the restricted distribution medical product; and denying by the controller based on the unsuccessfully performed electronic de-selection algorithm, the second or subsequent purchase request of the restricted distribution medical product, without intervention between the purchaser and a licensed practitioner, when the purchaser failed to successfully complete the electronic de-selection process.

* * * * *